(12) United States Patent
Kato et al.

(10) Patent No.: US 7,692,361 B2
(45) Date of Patent: Apr. 6, 2010

(54) ACTUATOR AND MATERIAL FOR THE ACTUATOR

(75) Inventors: Midori Kato, Kawagoe (JP); Masayoshi Ishibashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 979 days.

(21) Appl. No.: 11/338,740

(22) Filed: Jan. 25, 2006

(65) Prior Publication Data
US 2006/0261709 A1 Nov. 23, 2006

(30) Foreign Application Priority Data
May 19, 2005 (JP) .............................. 2005-146337

(51) Int. Cl.
*H01L 41/08* (2006.01)
(52) U.S. Cl. .................. 310/328; 310/800; 310/365
(58) Field of Classification Search ................ 310/800, 310/307, 306
See application file for complete search history.

(56) References Cited

U.S. PATENT DOCUMENTS

| | | | | |
|---|---|---|---|---|
| 6,067,797 | A * | 5/2000 | Silverbrook | ................ 60/528 |
| 6,522,237 | B1 * | 2/2003 | Ito et al. | .................... 338/22 R |
| 6,628,040 | B2 * | 9/2003 | Pelrine et al. | ............... 310/307 |
| 7,064,473 | B2 * | 6/2006 | Ishibashi et al. | ............ 310/330 |
| 7,327,067 | B2 * | 2/2008 | Ishibashi et al. | ............ 310/311 |
| 7,449,818 | B2 * | 11/2008 | Kato et al. | ................... 310/331 |
| 2005/0103706 | A1 * | 5/2005 | Bennett et al. | ......... 210/500.27 |
| 2007/0120444 | A1 * | 5/2007 | Kato et al. | ................... 310/330 |

FOREIGN PATENT DOCUMENTS

| | | |
|---|---|---|
| JP | 02-020586 | 7/1988 |
| JP | 02-155955 | 12/1988 |
| JP | 02-242847 | 3/1989 |
| JP | 06-006991 | 6/1992 |
| JP | 11-159443 | 11/1997 |
| JP | 2005176412 | 12/2003 |

OTHER PUBLICATIONS

Masayoshi Ishibashi et al., "An Extensional Actuator Using Composites Based on Ionic Polymer and Minute Carbon Particles", Polymer Preprints, Japan, vol. 53, No. 1 (2004) 1 page in Japanese with 1 page English translation.

* cited by examiner

*Primary Examiner*—J. SanMartin
(74) *Attorney, Agent, or Firm*—Stites & Harbison PLLC; Juan Carlos A. Marquez, Esq.

(57) ABSTRACT

A material for an actuator is provided which is reduced in weight, can be micro-miniaturized and can be used stably in a gas phase such as in atmospheric air safely, and an actuator using the material is provided. The material used for the actuator comprises a material formed by mixing fine conductive particles with a polymer material having a large absolute value of thermal expansion coefficient.

15 Claims, 17 Drawing Sheets

FIG.1A
FIG.1B
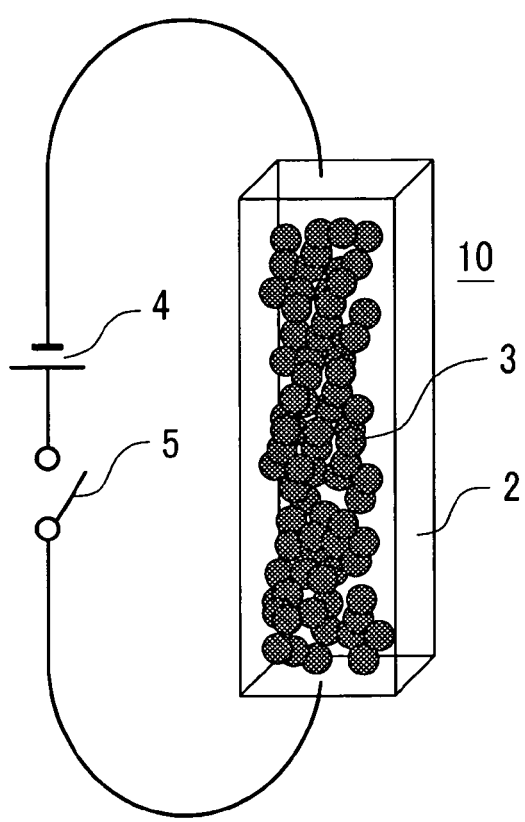
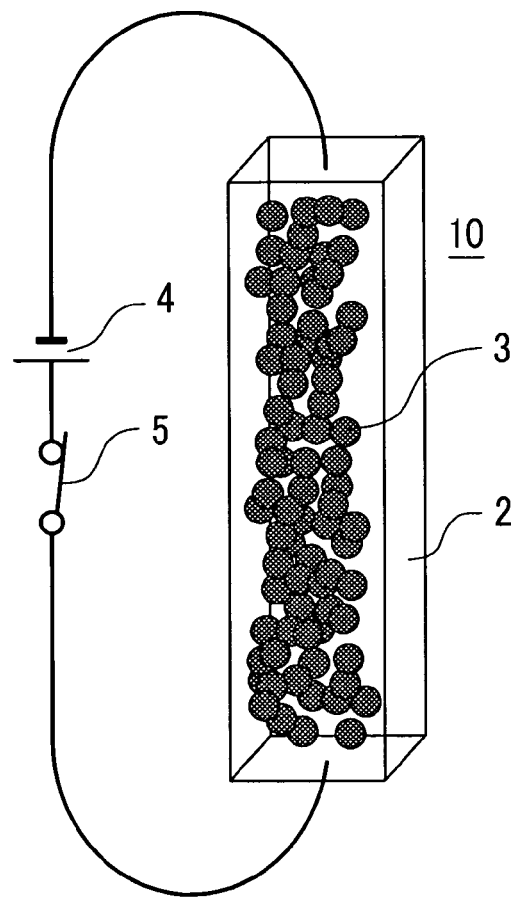

FIG.2A
FIG.2B
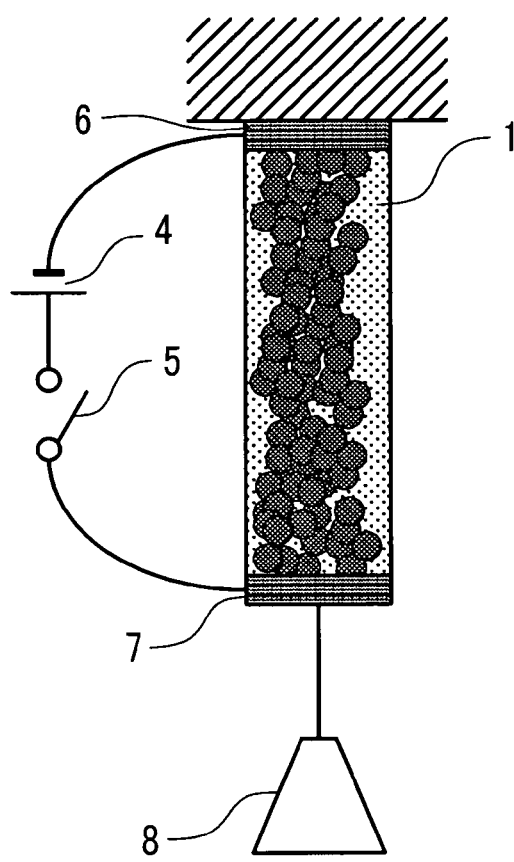
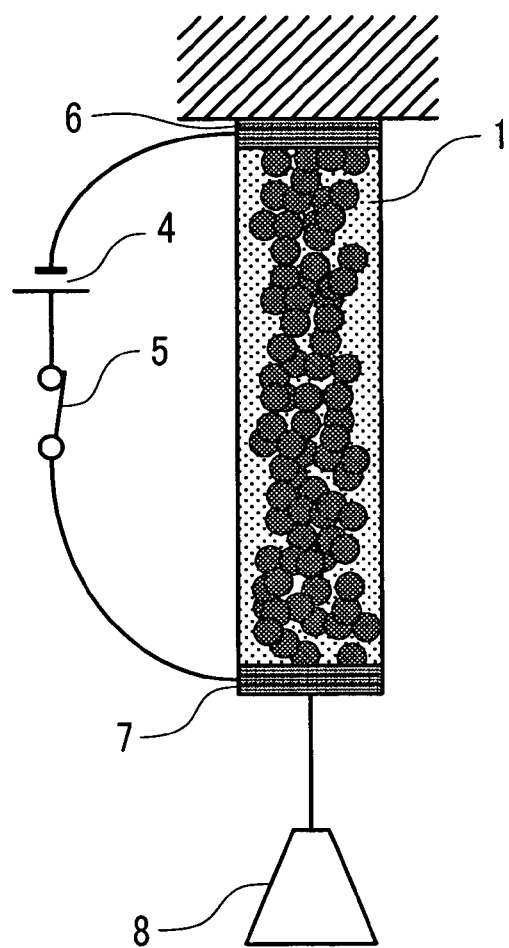

90

91

100

101

ACTUATOR AND MATERIAL FOR THE ACTUATOR

CLAIM OF PRIORITY

The present application claims priority from Japanese application JP 2005-146337 filed on May 19, 2005, the content of which is hereby incorporated by reference into this application.

BACKGROUND OF THE INVENTION

1. Field of the Invention

The present invention relates to an actuator module reduced in weight and capable of causing deformation such as expansion and contraction, bending, or the like repetitively by electric signals, and a material used therefor.

2. Description of the Related Art

Medical or nursing fields require safety actuators that can be micro-miniaturized and reduced in weight and that are flexible and operated at a low driving voltage for the application use of active catheters, endoscopes, rehabilitation aids, powered suits, artificial organs, etc. Further, paper displays and portable haptic devices for which a new demand will be expected in the future require actuators capable of attaining complicate movements in a small space in addition to the properties described above. As described above, not only actuators that can generate large stresses and high-speed response and can be controlled with high accuracy as usual but also actuators that can be micro-miniaturized and reduced in weight, and that is flexible and safe attaching to the boty (low driving voltage) will be necessary in the future.

For the actuators that can be micro-miniaturized, actuators in which a material per se can deform repetitively by electric signals are more suitable than those requiring assembling of parts such as an electromagnetic motor used usually. Actuators well-known at present in which the material per se deforms repetitively include a piezo actuator utilizing the piezo effect of ferroelectrics and an SMA actuator utilizing the phase transition of a shape-memory alloy (SMA). However, they have good and bad points in view of the driving voltage, the weight, and the durability.

As the actuator using the material that is deformed by electric signals, several kinds of actuators utilizing organic materials that deform by electric signals have been proposed in recent years, separately from the existent actuators described above. Since such actuators use organic materials, they have an advantage of reduced weight. They include, specifically, polymer actuators represented typically, for example, by a conductive polymer actuator using a conductive polymer such as polyaniline or polypyrrole for the material (Patent Document 1: JP-A No. 02-20586), an ionically conductive polymer actuator using an ionically conducting polymer as the material (Patent Document 2: JP-A No. 06-6991), a fine conductive particles mixed ionic polymer actuator in which fine conductive particles are bound with an ionic conductive polymer (Non-Patent Document 1: "Expanding actuator using ionic conductive polymer, by Masayoshi Ishibashi, Midori Kato, in 53th Annual Meeting of the Society of Polymer Science, Japan, 2004, IPA155), an actuator utilizing thermal deformation upon molecular desorption of conductive polymer (Patent Document 3: JP No. 3131180) and an actuator of using a material formed by mixing fine conductive particles to a shape memory resin (Patent Document 4: JP-A No. 02-242847, Patent Document 5: JP-A No. 02-155955).

SUMMARY OF THE INVENTION

The actuator utilizing the organic material that deforms depending on electric signals is reduced in the weight and can be easily micro-miniaturized; however, it involves several problems in view of operating circumstance and controllability. For example, most of polymer actuators conduct expanding and contracting operation only in an electrolyte solution by applying a voltage to counter electrodes disposed in the same electrolyte solution. Accordingly, the application use of the actuator is restricted to the inside of a body or in sea water and, to operate the actuator in a gas phase such as in atmospheric air, it is necessary to add a component such as packaging.

On the other hand, an actuator that utilizes the deformation by molecular desorption of a conductive polymer can operate in a gas phase. Since deforming by desorption of molecules such as of water, however, the actuator involves a problem in that the operation greatly depends on the surrounding circumstance such as humidity and the response is slow as well. For the material providing a shape memory resin with electric conductivity, since the deformation of the material is basically irreversible and does not repeat deformation in accordance with input electric signals, some or other devices are necessary for obtaining the operation as the actuator.

It is an object of the present invention to provide an actuator that can be used stably in a gas phase such as in air with safety, and can be micro-miniaturized, controlled satisfactorily, and reduced in weight.

Since a polymer material of high thermal expansion coefficient is an insulator, control of the temperature by heating under electric supply is difficult. In addition, since the material such as a metal of high electric conductivity has small thermal expansion coefficient, it is difficult to obtain large expansion and contraction within a practical range of temperature. In the invention, to attain the forgoing object, an actuator uses a material of high thermal expansion coefficient and high electric conductivity. The actuator according to the invention conducts self heat generation by electric supply to the actuator material and conducts expanding and contracting operation by utilizing the deformation of the material due to large thermal expansion and contraction caused by the change of the temperature.

The invention can provide a light weight and flexible actuator that can be used stably in a gas phase such as in air with safety and can be miniaturized, and that has good controllability.

BRIEF DESCRIPTION OF THE DRAWINGS

FIG. 1A is a diagram schematically showing the state of an actuator material before voltage is applied thereto;

FIG. 1B is a diagram schematically showing the state of the actuator material when the voltage is applied thereto;

FIGS. 2A and 2B are diagrams for explaining the basic operation of an actuator according to the invention using deformation of the actuator material as described for FIG. 1 by heating under electric supply;

FIGS. 6A and 6B are cross sectional views showing the concept of an actuator module structure of Embodiment 2 in which FIG. 6A illustrates the state of the actuator module before voltage is applied thereto and FIG. 6B illustrates the state of the actuator module when the voltage is applied thereto;

FIGS. 7A to 7C are conceptional views showing the form of an actuator module structure utilizing the V-shaped structure in which FIG. 7A is a perspective view for the outer profile of an actuator module using the V-structure as viewed obliquely from above, FIG. 7B is a cross-sectional view of an actuator module showing the state of lowering a pin in a case where voltage is not applied to the actuator module, and FIG. 7C is a cross sectional view of the actuator module showing the state of expanding the actuator film by applying a voltage to the actuator module to move the pin upward;

FIGS. 11A and 11B are explanatory upper views for the actuator module in which expanding and contracting operation of the actuator film described for Embodiment 1 is converted to bending operation in which FIG. 11A is a schematic perspective view illustrating the state before application of voltage to the actuator module 110 and FIG. 11B is a schematic perspective view for the state of applying the voltage to the actuator module 110;

DESCRIPTION OF THE PREFERRED EMBODIMENT

Figure 3:
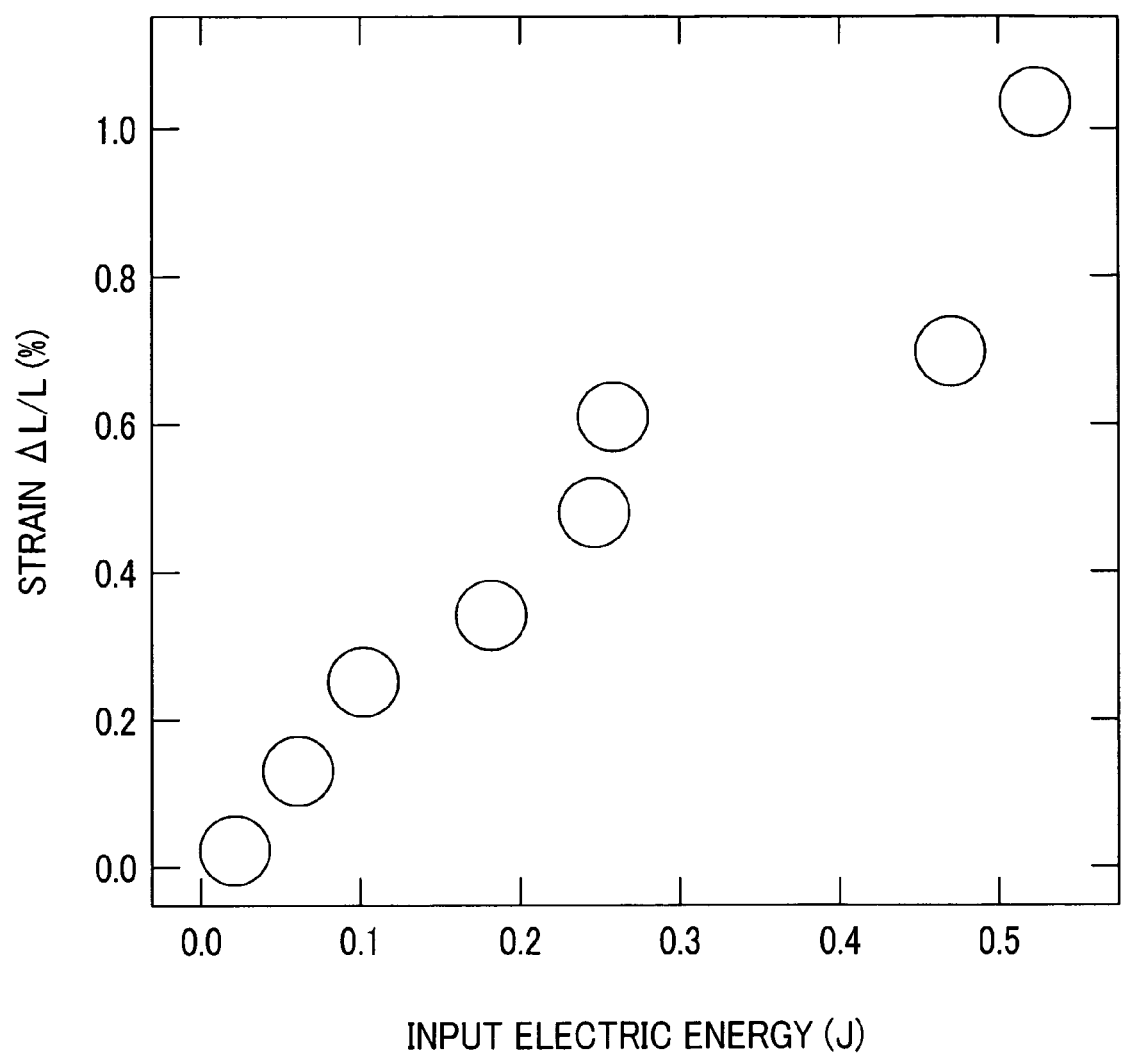
FIG. 3 is a graph showing the relationship between the strain of an actuator film 1 and electric energy input to the film.

According to the invention, since a material formed by mixing fine conductive particles with a polymer material having high thermal expansion coefficient is used for an actuator, electric conductivity is applied to the polymer material insulative by nature and self heat generation by electric supply and large deformation caused thereby can be enabled. Repetitive expanding and contracting operation is possible by conducting deformation at a temperature within a range of not causing plastic deformation under loading.

Conditions for obtaining a large displacement in the actuator according to the invention are to be described. The actuator of the invention utilizes the deformation by thermal expansion. Generally, the amount of deformation $\Delta L$ by thermal expansion of an object with a length L is in proportion with the temperature change $\Delta T$ and the proportional constant is a coefficient of linear thermal expansion $\alpha$. That is, they are in the relation shown by equation (1):

$$\Delta L = \alpha \times \Delta T \times L \tag{1}$$

In the actuator of the invention, the temperature of the actuator changes depending on the Joule heat generated by electric supply. Generally when a certain voltage is applied to a substance, assuming the electric resistance R is constant during application of the voltage, the Joule heat E generated during the time t is expressed as in equation (2):

$$E = V^2/R \times t \tag{2}$$

in which the resistance R is represented by using the electric conductivity $\kappa$ as in equation (3):

$$R = 1/\kappa \times L/S \tag{3}$$

in which S is a cross sectional area of the substance. Accordingly, based on equations (2) and (3), the Joule heat E generated by the application of the voltage is as shown in equation (4):

$$E = (\kappa \times S \times V^2 \times t)/L \tag{4}$$

On the other hand, the relationship between the Joule heat E and the temperature increase $\Delta T$ of the substance caused thereby can be written as in equation (5) assuming the specific heat of the substance as "c", the specific gravity as $\sigma$, and the energy loss caused by radiation or heat conduction as E'.

$$E - E' = c \times \sigma \times S \times L \times \Delta T \tag{5}$$

Accordingly, based on equations (5) and (4), the temperature increase $\Delta T$ can be written as in equation (6).

$$\Delta T = (\kappa \times V^2 \times t - E' \times L/S)/(c \times \sigma \times L^2) \tag{6}$$

Based on equations (6) and (1), the deformation amount $\Delta L$ is as shown in equation (7).

$$\Delta L = \alpha \times (\kappa \times V^2 \times t - E' \times L/S)/(c \times \sigma \times L) \quad (7)$$

Accordingly, it can be seen that the deformation amount $\Delta L$ increases in a material having a large thermal expansion coefficient $\alpha$, a high electric conductivity $\kappa$ and a small specific gravity $\sigma$.

Table 1 shows typical values for the material constants with respect to metal, ceramic, polymer material, and the material of the invention. Further, Table 1 also shows the tensile strength as the mechanical characteristic of the material. In a case of an actuator of the type where the material per se deforms, the force exceeding the limit at which the material per se is broken can not be outputted. That is, the maximum force generated as the actuator depends on the tensile strength of the material.

TABLE 1

|  | Coefficient of linear thermal expansion $\alpha$ ($\times 10^{-5}$/K) | Electric conductivity $\kappa$ (S/cm) | Specific gravity $\sigma$ | Tensile strength (MPa) |
| --- | --- | --- | --- | --- |
| Metal | 1-2 | $10^5$-$10^6$ | 2-20 | 100-1000 |
| Ceramic | 0.2-0.6 | $10^{-14}$-$10^{-11}$ | 3 | 30-50 |
| Polymer material | 1-20 | $10^{-15}$-$10^{-8}$ | 0.9-1.5 | 4-100 |
| Invention | 1-100 | $10^{-1}$-$10^{-3}$ | 0.5-5 | 0.3-200 |

Since the material of the invention mainly comprises a polymer material, the expansion coefficient is large and the specific gravity is small. Further, since the material is mixed with the fine conductive particles, the electric conductivity is high to some extent. Accordingly, a practical actuator can be provided which has large deformation by heating under electric supply. Further, since it has not so high the electric conductivity as metal, the material also has a merit of not requiring large current for heating without using a super thin film. A method of mixing fine particles with the polymer material is often practiced with an aim of improving the mechanical strength of the polymer material. Therefore, also the tensile strength of the material according to the invention is larger than that of the polymer material.

The present invention is to be described by way of examples with reference to the drawings.

Embodiment 1

In Embodiment 1, the concept of the basic operation of an actuator according to the invention and a manufacturing method thereof are to be described. At first, a description is to be made of the deformation of an actuator material when a voltage is applied to the actuator material constituting the actuator of the invention.

FIG. 1A schematically shows the state of an actuator material before voltage is applied thereto and FIG. 1B schematically shows the state of the actuator material when the voltage is applied. In the figures, are shown a polymer material 2 of large thermal expansion coefficient, fine conductive particles 3, and an actuator material 10 in which the fine conductive particles 3 are dispersed in the polymer material. There are also shown a power source 4 and a switch 5. Current can be supplied or stopped to the polymer material 10 by turning the switch 5 on or off. When a voltage of the power source 4 is applied to the actuator material 10 with the switch 5 being turned on, the temperature of the actuator material 10 increases by the Joule heat, and isometric deformation is caused in the actuator material 10 in accordance with the thermal expansion coefficient (FIG. 1B). On the other hand, when the switch 5 is turned off, electric supply to the actuator material 10 is stopped, the temperature is lowered and the actuator material 10 resumes an original shape (FIG. 1A). It will be apparent that the shape change can be conducted in a gas phase such as in atmospheric air. The actuator of the invention conducts expanding and contracting operation by utilizing the phenomenon.

Specifically, fine carbon particles with a size of about 40 nm were used as the fine conductive particles 3 and a perfluorosulfonic acid-copolymer was used as the polymer material 2, and they were mixed at a mixing ratio of about 1:5 by weight ratio to form the actuator material 10. In this case, when the application voltage was controlled to optimize the temperature of the actuator material 10 during electric supply, a strain of about 2% at the maximum was obtained. The strain is a quantity represented by $\Delta L/L$ assuming the entire length of the actuator before voltage application as L and the expansion of the actuator upon voltage application as $\Delta L$.

The perfluorosulfonic acid-copolymer used in the polymer material 2 is a fluoro polymer, which is a material of high thermal expansion coefficient excellent in the heat resistance. By mixing and dispersing the fine carbon particles with the material, an actuator material 10 of high thermal expansion coefficient and high electric conductivity can be formed. The actuator material 10 of Embodiment 1 has a coefficient of linear thermal expansion of 0.0001/K at 100° C., an electric conductivity of 1 siemens/cm, and a glass transition temperature of 230° C. Since the strain of the actuator material 10 by voltage application is about 2%, it can be estimated that the temperature of the actuator material 10 increases to about 220° C. by the voltage application.

In a case of conducting the deformation of the actuator material by heating under electric supply as described with reference to FIGS. 1A and 1B in a state of applying a load such as a weight on the actuator material, the load can be moved reversibly within a certain range of the load, so that the material can be used as the actuator.

FIGS. 2A and 2B are views for explaining the basic operation of the actuator according to the invention utilizing the deformation by heating under electric supply of the actuator material as described in FIG. 1. FIG. 2A shows a state before application of the voltage while applying only a load such as a weight to an actuator film 1, and FIG. 2B shows a state of applying the voltage to the actuator film 1 while applying the load. The actuator film 1 is formed as a film shape being longer on one side of the actuator material 10, so that the deformation by the voltage application is small and negligible, compared with that in the longitudinal direction, in the portion other than the longitudinal direction of the film. An electrode 6 and an electrode 7 for applying voltage are disposed at both longitudinal ends of the actuator film 1, to which an external power source 4 and a switch 5 are connected in series therewith. Further, one end of the actuator film 1 is fixed to a wall or the like and the other end thereof is subjected to a load 8 in the direction where the actuator film 1 is pulled (FIG. 2A). In this case, the magnitude of the load 8 should not exceed the tensile strength of the actuator film 1. As with the case of FIG. 1B, when the switch 5 is turned on in this state and a voltage from the power source 4 is applied to the actuator film 1, the actuator film 1 expands thermally by the temperature increase by heating under electric supply, that is, the film elongates (FIG. 2B). When the switch 5 is turned off in this state, the actuator film 1 lowers in temperature and contracts again (FIG. 2A). In this case, along with expansion and contraction of the actuator film 1, the load 8 moves vertically. That is, the expanding and contracting operation of the actuator film 1 can be taken out as work of the vertical motion. In a case of restricting the temperature upon electric supply to the actuator film 1 to a value lower than the glass transition temperature, the expanding and contracting operation of the actuator film 1, that is, the vertical motion of the load by heating under electric supply can be repeated reversibly.

In a case of using the actuator film 1 measuring 1 cm in length, 2 mm in width, and 120 µm in thickness, attaching a weight of 50 g as the load 8 thereto and applying thereto a rectangular wave voltage at an amplitude of 22 V and at a frequency of 1 Hz, the strain of the actuator film 1 per 1 pulse was about 2%. That is, the load 8 of 50 g weight could be moved vertically for about 200 µm at a frequency of 1 Hz. In this example, the force generated by the actuator film 1 is about 2 MPa. The actuator material of Embodiment 1 can generate a force of about 3 MPa at the greatest.

Further, the actuator film 1 of Embodiment 1 conducts expanding and contracting operation in accordance with the frequency also when a rectangular voltage at 10 Hz was applied thereto. Further, when it was caused to actuate the expanding and contracting operation for 100,000 cycles (repeating the state of FIGS. 2A and 2B), the value of the strain was not changed from the initial state and the actuator film was operated stably.

FIG. 3 shows the relationship between the strain of the actuator film 1 per 1 pulse and the electric energy input to the film upon application of a rectangular wave voltage with an amplitude of 15 V and at a frequency of 1 Hz. It can be seen that a proportional relation is established between the strain of the actuator film 1 and the electric energy input to the film. Accordingly, the magnitude of the expansion and contraction of the actuator film 1 can be easily controlled electrically by controlling the input electric energy. While a DC power source was used as the power source in this case, since the strain of the actuator film 1 is in proportion to the input electric energy, it can be controlled in the same manner by the control for the input electric energy also by using an AC power source. In any of the cases, while it is the simplest to conduct control by the voltage applied to the actuator film, it will be apparent that current control is also possible.

Further, the electric resistance of the material according to the invention is a resistance of the fine conductive particles mixed in the polymer and the resistance between the fine particles. When the actuator film 1 deforms, therefore, the resistance between the fine particles changes and, as a result, the resistance of the actuator film also changes. By monitoring the same, the deformation of the actuator film 1 can be estimated. Accordingly, the deformation can be controlled accurately by applying feed back to the application voltage by using the resistance value.

When a constant voltage continuously applied to the actuator film 1, the deformation amount of the film is converged to a predetermined value unless the temperature of the film exceeds the glass transition temperature or the melting point or decomposes point of the material for the actuator film. This is because the input electric energy and the energy emitted by radiation, conduction, convection, etc. are in a balanced state. Once the balanced state is reached, the deformation amount can be maintained constant.

In a case where the polymer material 2 used for the actuator film 1 has a polymeric hygroscopicity, when the film is left at room temperature, it contains surrounding humidity to swell somewhat more greatly compared with the dried state. However, by always supplying a low current to the film, the temperature of the film can be elevated to evaporate the water content and keep the film in a dried state irrespective of the surrounding humidity. By using the method described above, the deformation amount of the actuator film can be controlled accurately not depending on the surrounding humidity even in a case of using hygroscopic material.

As also described previously, in a case where the electric energy input to the actuator film 1 is large and the temperature of the film exceeds the glass transition temperature of the material for the actuator film 1, the mechanical characteristic of the film is remarkably deteriorated. That is, the tensile strength is lowered to form an extremely soft state and the film causes plastic deformation even by a small load and no more resumes the original shape. In such a state, it can not operate as the actuator. Since the amount of deformation by the thermal expansion is larger as the temperature difference is larger, the maximum deformation amount in the invention is restricted by the glass transition temperature of the actuator film 1 as a determinative factor. Since the actuator film 1 is a composite material of the polymer material 2 and the fine conductive particles 3, the glass transition temperature of the film depends on the glass transition temperature of the polymer material 2. Accordingly, when a material of high glass transition temperature is used for the polymer material 2, the workable temperature range is extended accordingly and, consequently, the deformation amount of the actuator film 1 can also be made larger.

However, depending on the type of the polymer material such as a crystalline polymer, the polymer material may not have a glass transition point. In this case, it is necessary to control the input energy so that the operation is not conducted at a temperature exceeding the melting point or the decomposition point of the material. Also in this case, the melting point or the decomposition point of the material for the actuator film 1 depends on the melting point or the decomposition point of the polymer material 2 forming the actuator film. Therefore, the workable temperature range can be extended, that is, the deformation amount of the actuator can be made larger by using a material of high melting point or decomposition point as the polymer material 2.

Further, to greatly deform the actuator film 1 of the invention, it is necessary that not only the heat resistance but also the expansion coefficient are high. That is, polymer materials of high softening point and high thermal expansion coefficient are suitable to the polymer material 2 used in the actuator film 1. The polymer materials described above include, in addition to the perfluorosulfonic acid-copolymer used for the polymer material 2 in Embodiment 1, acrylonitrile-butadiene-styrene copolymer, polymethacrylate ester such as acrylic resin, polyethylene terephthalate, polyamide, polyoxymethylene, polytetrafluoroethylene, polystyrene, polycarbonate, and polyalkenes such as polycyclohexylethylene, polyacrylic acid, and polymethacrylic acid, etc. They can be used as the polymer material constituting the actuator film. The coefficient of linear thermal expansion of the polymer materials described above is generally from 0.00001/K to 0.0002/K. Accordingly, the coefficient of linear thermal expansion of the actuator film using them as the constituent material is also 0.00001/K or more. On the contrary, in a case where the coefficient of linear thermal expansion is excessively large, since the deformation is large and the burden on the material increases, the coefficient of linear thermal expansion is appropriately at about 0.001/K or less.

While fine carbon particles with a diameter of 40 nm are used for the fine conductive particles 3 of the actuator film 1 in Embodiment 1, fine conductive carbon particles of a larger size, carbon nanotubes, fine metal particles such as of gold, silver, platinum, copper, and nickel, or mixtures thereof can also be used. The electric conductivity of the actuator film can be changed by changing the kind of the fine conductive particles and the mixing ratio with the polymer material. In a case where the electric conductivity is low, a high voltage is necessary for driving. On the other hand, in a case where the electric conductivity is excessively high, supply of large current is required and a usual power source can not be used. The practical value of the electric conductivity is from 0.1 to 1000 siemens/cm.

Generally, when fine particles are mixed with the polymer material, the mechanical strength of the composite material increases. Increase of the strength by about twice can be expected also depending on the type and the amount of the material to be mixed. The tensile strength of the actuator film of the invention as the composite material has a tensile strength about twice the polymer material as the constituent material, that is, about 200 MPa at the maximum. On the other hand, as described previously, the maximum stress generated from the actuator depends on the tensile strength of the material. Accordingly, a material of excessively low tensile strength does not work as an actuator. Therefore, a tensile strength of 0.3 MPs or more is necessary as a practical value.

By changing the kind and the mixing ratio of the polymer material and the fine conductive particles, an actuator film having the coefficient of linear thermal expansion, the electric conductivity and the tensile strength as described above can be manufactured. In this case, the specific gravity of the actuator varies in accordance with the type and the mixing ratio. Since the fine carbon particles used in Embodiment 1 have an extremely low bulk density, when the fine particles are mixed with the polymer, the specific gravity of the mixed material is less than the specific gravity of the polymer. However, in a case where the amount of the fine particles is excessively large relative to the polymer, a film can no more be formed. Since the specific gravity of the mixed material in this instance is about 0.5, it is desirable that the specific gravity of the mixed material be 0.5 or more. Further, since the object of the invention is to provide an actuator of a reduced weight, a material of a large specific gravity such as metal does not conform to the purpose of the invention. Accordingly, a material with the specific gravity of 5 or less is practical.

By using the polymer material and the fine conductive particle material described previously and optimizing the mixing ratio, an actuator film having a heat resistance of 100° C. or higher, a coefficient of linear thermal expansion of from 0.00001/K to 0.0001/K, an electric conductivity of from 0.1 to 100 siemens/cm, a specific gravity of from 0.5 to 5, and a tensile strength of from 0.3 to 200 MPa can be manufactured easily.

Physical properties of several actuator films manufactured from polymer materials and fine conductive particles in combination are shown in Table 2 by way of example.

Further, while the description has been made for FIG. 1 and FIG. 2 by using an actuator material that expands by electric supply, an actuator that contracts by electric supply can be manufactured by using a material having a negative thermal expansion coefficient such as polyparaphenylene benzobisoxazole as the polymer material 2.

A method of manufacturing the actuator film of Embodiment 1 is to be described with reference to FIGS. 4A to 4D. FIGS. 4A to 4D are conceptional views showing a step for the method of manufacturing the actuator film of Embodiment 1.

Figure 4A:
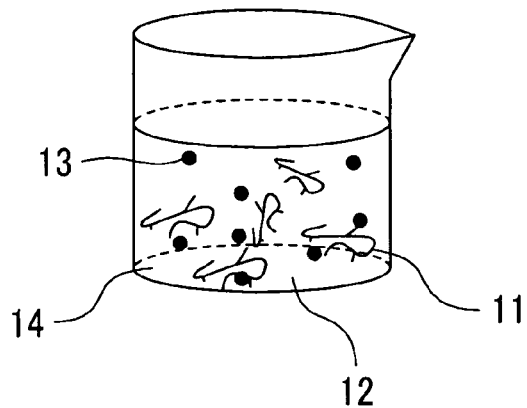
FIGS. 4A to 4D are conceptional diagrams showing the steps of a manufacturing method of an actuator film of Embodiment 1.

At first, fine conductive particles 13 are mixed at an optional ratio to a solution in which a polymer 11 is dispersed in a solvent 12 (liquid polymer dispersion) and stirred to prepare a fine particle-mixed solution 14 (FIG. 4A). In Embodiment 1, the liquid polymer dispersion is a solution formed by dispersing a perfluorosulfonic acid-copolymer by 5% to a mixed solvent of water and alcohol (mixing ratio 1:1), or a mixed solution of the solution described above and dimethyl formamide. Fine carbon particles with a diameter of about 40 nm are used for the fine conductive particles 13.

Figure 4B:
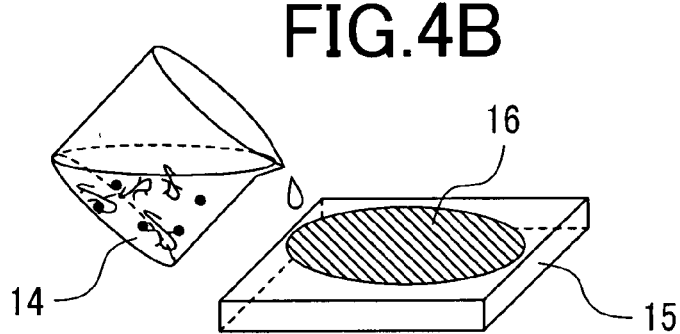

Then, the thus prepared fine particle-mixed solution 14 is coated on a substrate 15 and dried at a high temperature of 70° C., to prepare a mixed film 16 of the polymer and the fine conductive particles (thickness: 120 μm) (FIG. 4B). In Embodiment 1, a glass substrate is used for the substrate 15. Further, in Embodiment 1, while the drying temperature is set at 70° C., the drying temperature region can be from room temperature to 180° C. As the coating method, any of a cast method, a spin coating method, or a spray coating method can be used.

Figure 4C:
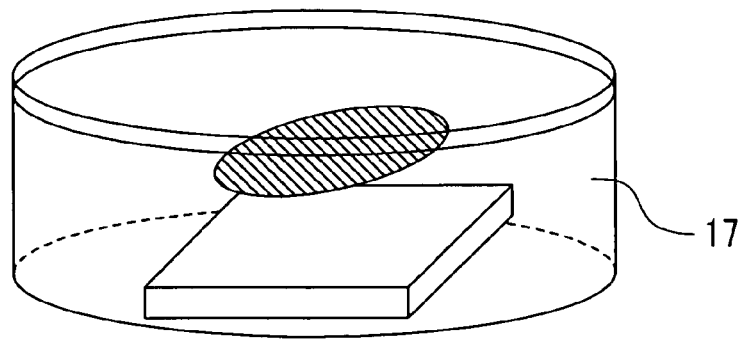

Then, the dried mixed film 16 of the polymer and the fine conductive particles is dipped in purified water 17 in a state of being deposited to the substrate 15 as it is. Then, the mixed film 16 of the polymer and the fine conductive particles swells and peels from the substrate 15 (FIG. 4C).

Figure 4D:

Finally, the peeled mixed film 16 of the polymer and the fine conductive particles is scooped and unnecessary portions are mechanically cut out to provide an arranged optional shape, thereby completing an actuator film 1 (FIG. 4D).

Figure 5:
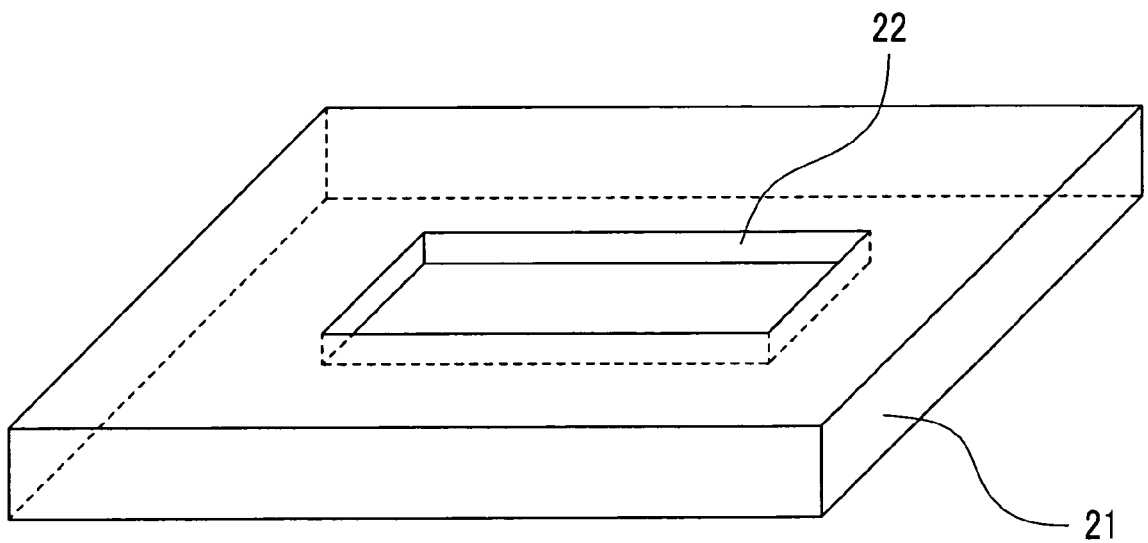
FIG. 5 is a perspective view of a substrate used for molding the actuator film by way of example.

In the shaping treatment in FIG. 4D, while the shape was arranged by mechanical cutting, the shape may also be arranged by dry etching using an oxygen gas, etc. Further, while the shape of the actuator film is arranged after peeling from the substrate 15, it may be arranged also before peeling. Further, as shown in FIG. 5, an actuator of a required shape can be obtained also by forming an indent 22 corresponding to the necessary shape of the actuator film 1 in the substrate 21, casting a mixed solution of the fine particles into the indent 22 and then drying and peeling the same.

Further, while the liquid dispersion of the polymer in which the polymer 11 is dispersed in the solvent 12 is used in FIG. 4, it can also be prepared, instead, by mixing and kneading the fine conductive particles to the polymer in the molten state. A

TABLE 2

| Polymer material | Fine Conductive particles | Weight ratio (polymer:fine particle) | Coefficient of linear thermal expansion α (×10⁻⁵/K) | Electric conductivity k(S/cm) | Specific gravity σ | Tensile strength (MPa) |
|---|---|---|---|---|---|---|
| Perfluorosulfonic acid-copolymer | Nickel (diameter: 1 μm) | 2:8 | 5 | 26 | 5 | 2 |
| Perfluorosulfonic acid-copolymer | Carbon (diameter: 5 μm) | 4:6 | 5 | 0.7 | 0.9 | 4 |
| Polymethyl methacrylate | Carbon (diameter 40 nm) | 3:7 | 4 | 1 | 0.6 | 50 | heat compression or melt extrusion method used for usual resin fabrication can be adopted for molding.

According to Embodiment 1, an actuator of an optional film shape capable of stable expanding and contracting operation by the application of voltage in atmospheric air can be manufactured easily.

Embodiment 2

Figure 6A:
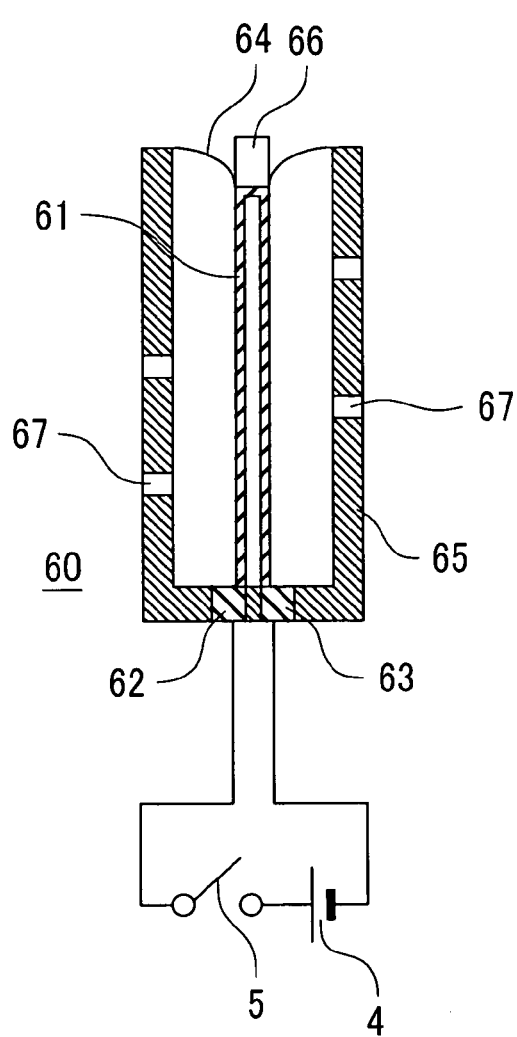
Figure 6B:
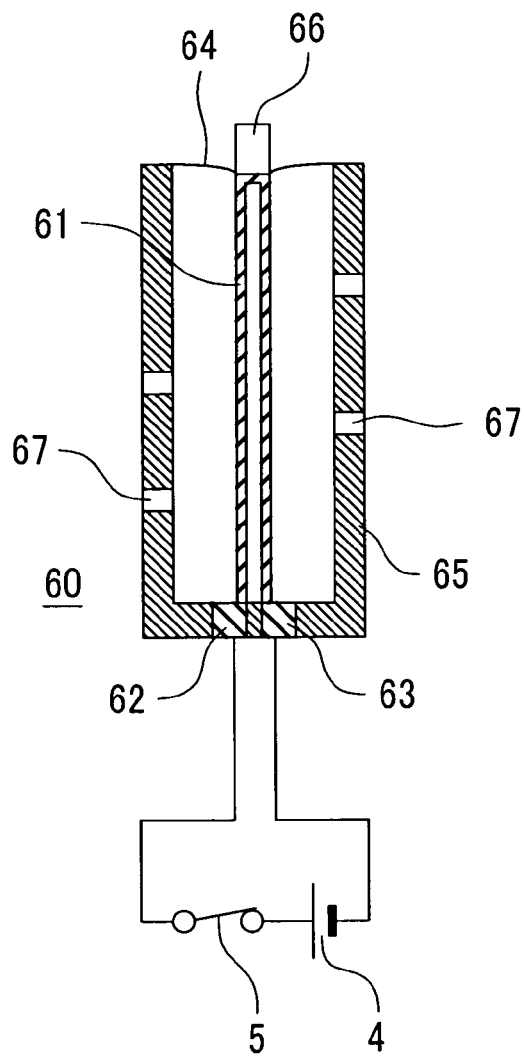

In Embodiment 2, an actuator module structure using the actuator of the invention and an actuator matrix utilizing the same are to be described with reference to FIGS. 6A to 8B. FIGS. 6A and 6B are cross sectional views showing the concept of the actuator module structure of the invention in which FIG. 6A is a cross sectional view of an actuator module in a state before application of a voltage and FIG. 6B is a cross sectional view of the actuator module in a state upon application of the voltage. In an actuator module 60, a stretchable member 64 is disposed in an open plane of an elongate box-shaped container 65, and electrodes 62, 63 are buried in the bottom of the container 65. An actuator film 61 turned back at the central portion thereof is disposed inside the container 65, the turned back portion is joined to the lower surface of the stretchable member 64 at the upper surface of the container 65, and both ends of the actuator film 61 are joined with the respective electrodes 62, 63. A pin 66 is joined to the rear face of the stretchable member 64 to which the actuator film 61 is joined such that it overlaps the actuator film 61. The actuator film 61 is adjusted in length so that it may always undergo tension by the stretchable member 64. One or more of heat dissipation holes 67 are punctured in the container 65. Instead of the heat dissipation hole, a structure may be adopted of attaching a Peltier device on the lateral surface inside the container 65 to cool the actuator film 61.

When a voltage is applied between the electrodes 62 and 63 of the actuator module 60, the actuator film 61 undergoing the tension from the stretchable member 64 can expand to move the pin 66 upward (FIG. 6B). Further, the pin 66 is moved downward again by lowering the value of the applied voltage or turning off the switch 5. In this way, the pin 66 can be moved vertically by the voltage signal.

One of methods of magnifying the movement of a expanding actuator of small strain uses a V-shaped structure. The V-shaped structure means a structure in which both ends of the expanding actuator are fixed and a load is applied to the central portion of the actuator perpendicularly thereto. Both ends of the actuator are fixed to a container such that the expanding actuator is straightened in a contracted state. Then, when the actuator is extended in this state, the central portion is distorted. When the distortion is taken out as a displacement in the direction perpendicular to the actuator by a load applied to the central portion, it is possible to obtain a value much greater than the displacement obtained by the expansion and contraction in the extending direction of the actuator at the open end of the actuator.

Figure 7A:
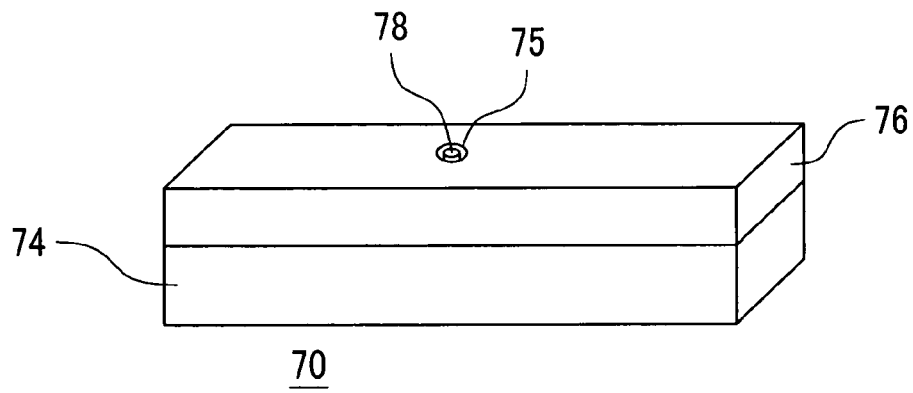
Figure 7B:
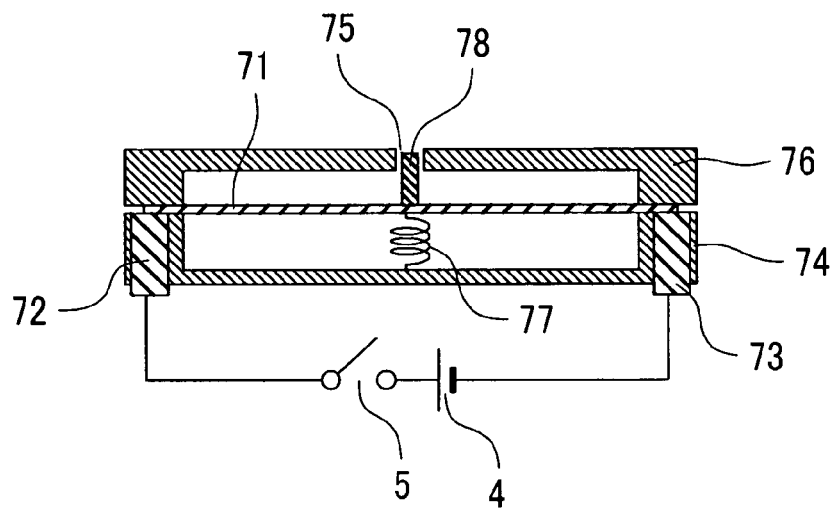
Figure 7C:
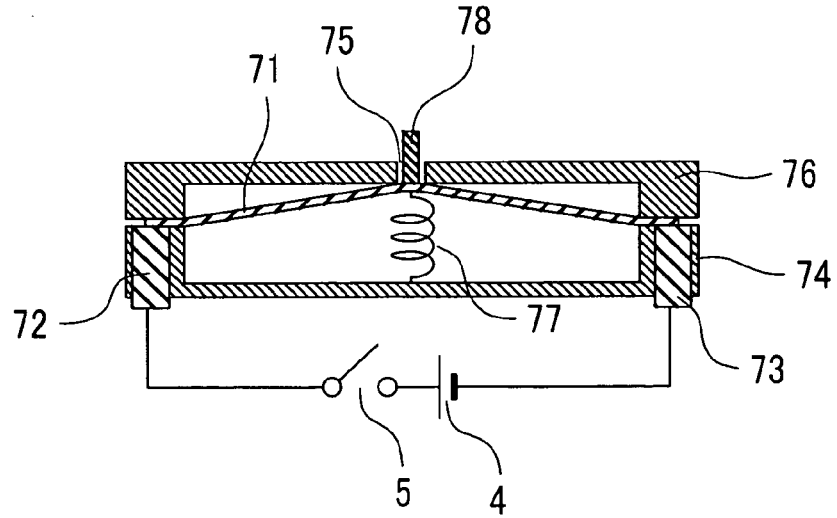

FIGS. 7A to 7C are conceptional views showing the state of an actuator module structure utilizing the V-shaped structure. FIG. 7A is an upper perspective view showing the outer profile of an actuator module using the V-structure, FIG. 7B is a cross sectional view of the actuator module showing the state in which the pin is lowered with no application of a voltage and FIG. 7C is a cross sectional view of the actuator module showing the state in which the pin is moved upward by extending the actuator film with application of the voltage to the actuator module.

An actuator module 70 has a configuration of joining a bottom container 74 and a lid 76, in which a pin 78 moves vertically through an opening 75 at the central portion of the lid 76. An actuator film 71 is disposed in the upper surface of the bottom container 74, and both ends of the actuator film 71 are connected with respective electrodes 72, 73 buried in the side wall of the bottom container 74. A spring 77 for exerting a force pushing the actuator film 71 upward is disposed to the central portion of the actuator film 71 between the film and the bottom of the bottom container 74. A pin 78 is disposed at a position opposite to the spring 77 in contact with the actuator film 71. Further, although not illustrated, one or a plurality of heat dissipating holes are perforated in the bottom container 74 and the lid 76. Further, instead of the heat dissipating hole, a structure may be adopted attaching a Peltier device at the bottom of the container 74 for cooling the actuator film 71.

The length of the pin 78 is adjusted such that the upper surface of the pin 78 is below the surface of the lid 76 before application of a voltage to the electrodes 72, 73, that is, before extension of the actuator film (FIG. 7B). When a voltage is applied to the electrodes 72, 73, the actuator film 71 is extended, the pin 78 is moved upward by the spring 77 and thus the upper surface of the pin 78 appears above the surface of the lid 76. Further, when the application of the voltage is interrupted or the value of the applied voltage is lowered, the pin 78 is lowered again. As described above, the pin 78 can be moved vertically depending on the voltage signal.

In the actuator module shown in FIG. 7, in a case of using the actuator film 71 of with a length of 1 cm and expanding and contracting the film at 2%, the pin 78 can be vertically moved by 1 mm.

The actuator module shown in FIG. 7 has a feature in that not only a large displacement can be taken out but also the actuator matrix can be easily formed by joining the respective wall surfaces of the bottom containers 74 together. Further, the actuator matrix composed of the actuator modules shown in FIG. 7 has an advantage that the displacement is large, as well as the thickness thereof can be decreased.

Figure 8A:
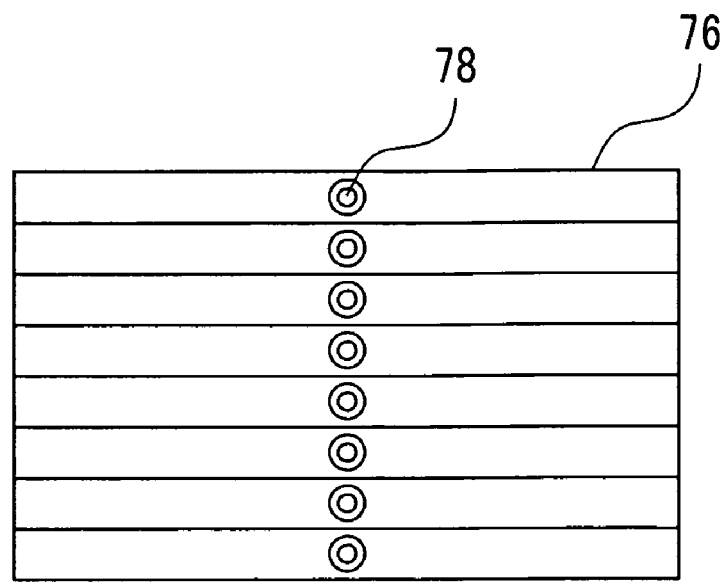
FIGS. 8A and 8B are conceptional upper plan views showing an actuator matrix using the actuator module shown in FIG. 7.
Figure 8B:
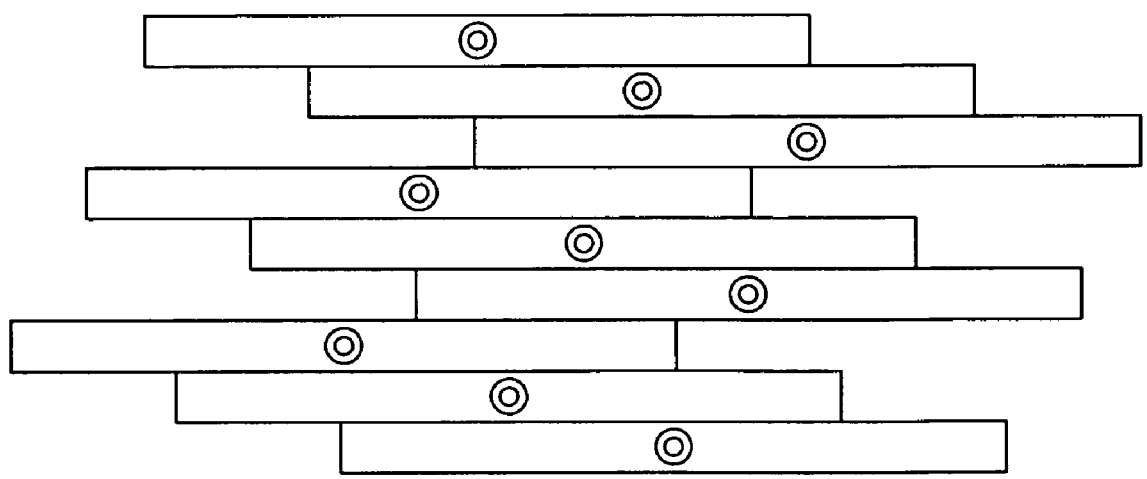

FIGS. 8A and 8B are conceptional upper plan views showing an actuator matrix using the actuator module shown in FIGS. 7A to 7C. FIG. 8A shows an example of a one-dimensional actuator matrix in which actuator module containers 74 are arranged such that its longitudinal lateral surfaces are parallel to one another and its pins 78 are aligned with one another. FIG. 8B shows an example of a two-dimensional actuator matrix in which actuator module pins 78 are arranged in a two-dimensional manner such that its longitudinal lateral surfaces are parallel to one another and are slightly displaced with one another.

Embodiment 3

Embodiment 3 proposes a Braille display device as one of portable haptic devices as an application example of the actuator module shown in Embodiment 2, as well as a Braille display system using the same, which is to be described with reference to FIGS. 9A, 9B, 10A and 10B.

A Braille cell is expressed as a unit in which protrusions each having a height of about 0.4 mm are arranged about 2.2 mm apart to constitute a 3×2 dot matrix. The Braille display device of Embodiment 3 is a device in which six pins are arranged as a 3×2 matrix and an optional pin can be moved vertically at 0.4 mm stroke in response to electric signals.

Figure 9A:
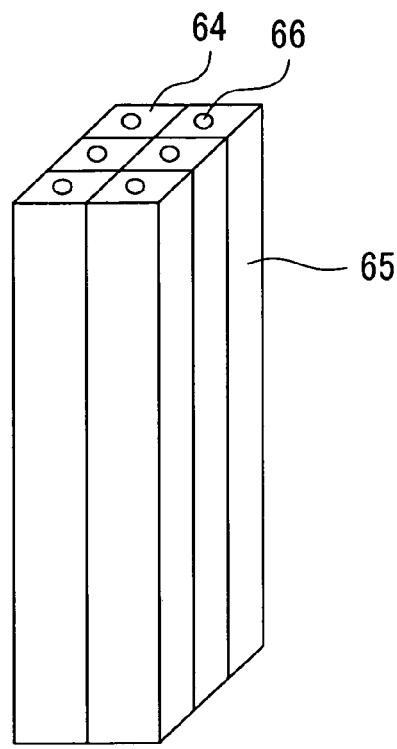
FIG. 9A is a conceptional perspective view showing the state of a Braille display device 90 using the actuator module described in FIG. 6 for Embodiment 2.
Figure 9B:
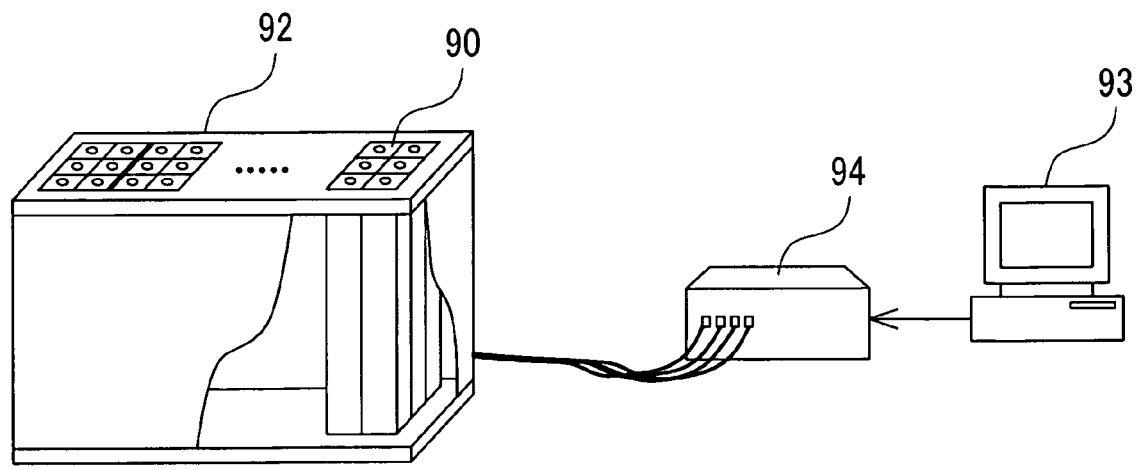
FIG. 9B is a conceptional perspective view of a Braille display system using the Braille display device 90.

A most simple Braille display device using the actuator module according to the invention is an actuator matrix using the actuator module 60 described in FIG. 6 for Embodiment 2 and arranging them in 3×2 arrangement. FIG. 9A is a conceptional view in which Braille display device 90 having actuator modules 60 arranged in 3×2 is viewed from above obliquely, and FIG. 9(B) is a conceptional view of a Braille display system 91 using the Braille display devices 90.

The actuator module 60 is configured as described below to meet the specifications of Braille.

(1) To arrange the pins about 2.2 mm apart, the cross section of the actuator module 60 as viewed from above is sized 2.2 mm×2.2 mm.

(2) Since it is necessary to move the pin vertically by 0.4 mm, the length of the actuator film 61 before turn back is set to about 40 mm and a voltage is applied such that the strain is 2%.

A Braille display system 91 includes a Braille display terminal 92 having a plurality of the Braille display devices 90, a control device 93 such as a central processing unit (CPU), and a driving signal generating device 94 connected to the control device. The driving signal generation device 94 is controlled by the instruction from the control device 93 to apply a voltage to necessary actuator modules. A sentence displayed by Braille can be read in this state by touching over the upper surface of the Braille display terminal 92. Since the Braille display device 90 using the invention is small in size and light in weight, also a small and light Braille display terminal can be attained. In FIG. 9, heat dissipating holes are not illustrated.

Figure 10A:
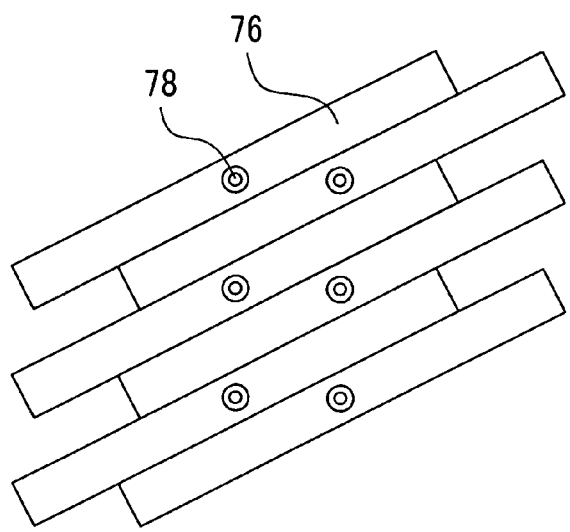
FIG. 10A is a conceptional upper plan view of a Braille display device 100 using the actuator module 70 described in FIG. 7 for Embodiment 2.
Figure 10B:
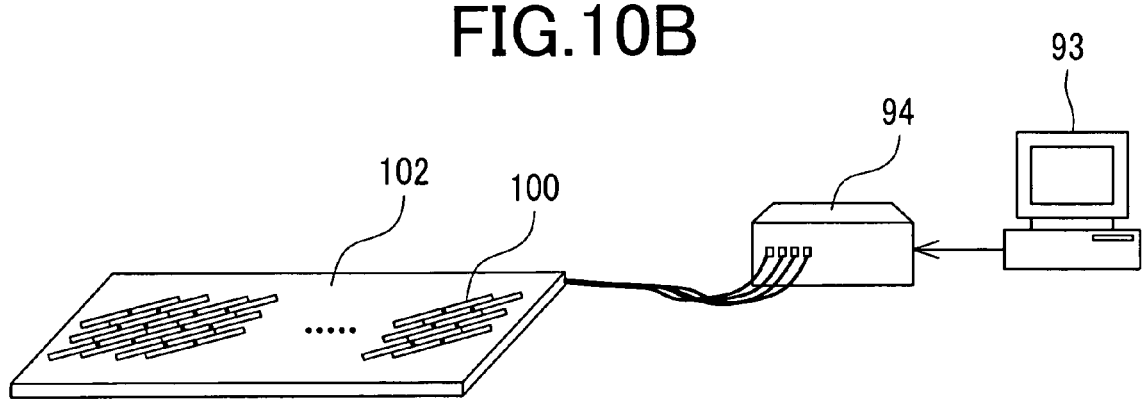
FIG. 10B is a conceptional view of the Braille display system 101 using the Braille display device 100.

FIG. 10A is a conceptional upper plan view showing the state of a Braille display device 100 in which the actuator modules 70 described for Embodiment 2 in FIG. 7 are arranged by 3×2, and FIG. 10B is a conceptional view of a Braille display system 101 using the Braille display device 100. To meet the specifications of the Braille, the actuator module is configured as below.

(1) To arrange the pins about 2.2 mm apart, the width of the actuator module viewed from above is set to 0.98 mm.

(2) Since it is necessary to vertically move the pin by 0.4 mm, the length of the actuator film 71 is set to about 4 mm.

By arranging the actuator modules by the number of 6 in the longitudinal direction of the actuator module so as to be alternately displaced by 1.96 mm each, a Braille display device in which Braille is displayed by the application of voltage to optional actuator modules can be obtained.

The Braille display system 101 is the same as the Braille display system 91 except for providing a Braille display terminal 102 having a plurality of the Braille display devices 100. Since the Braille display device 100 using the actuator module 70 is further reduced in thickness and in weight compared with the Braille display device 90 using the actuator module 60, the Braille display terminal 102 reduced in thickness and in weight can also be obtained.

Embodiment 4

In Embodiment 4, an actuator module in which the expanding and contracting operation of the actuator film described for Embodiment 1 is modified into a bending operation is to be described with reference to FIGS. 11A and 11B.

Figure 11A:
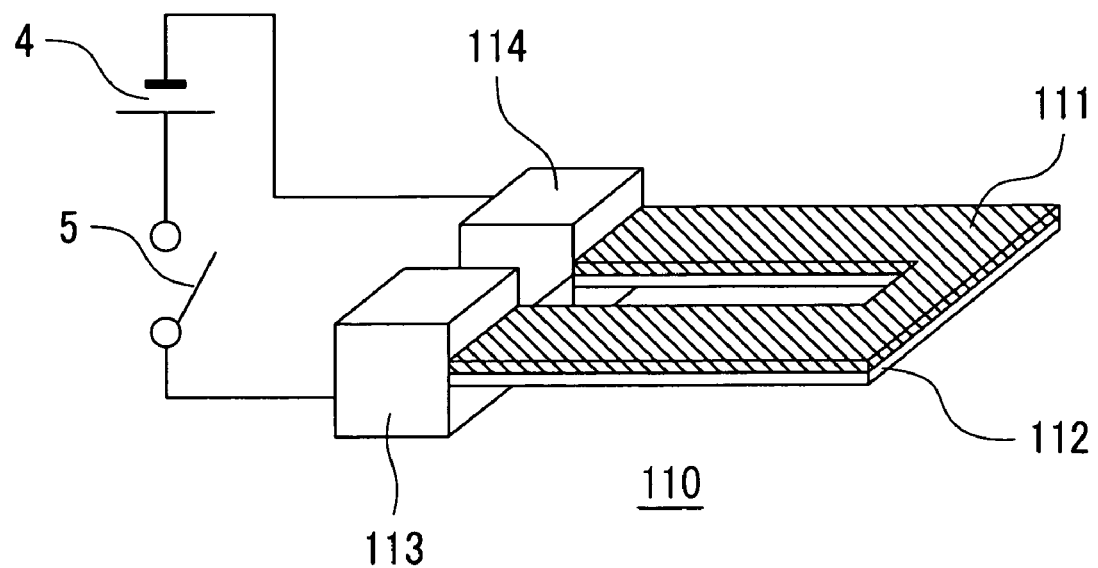
Figure 11B:
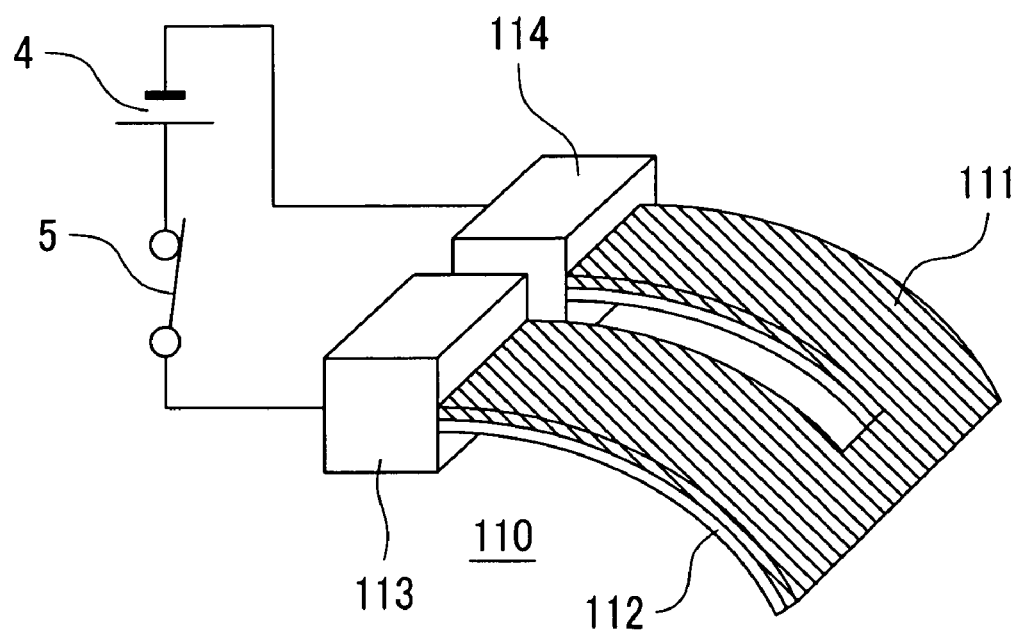

FIG. 11A is a schematic upper perspective view of an actuator module 110 in a state before application of a voltage, and FIG. 11B is a conceptional upper perspective view of an actuator module 110 in the state of applying the voltage. An actuator module 110 has a structure in which an actuator film 111 formed into a U-shape is adhered to an insulator film 112 formed into the identical shape with no displacement therebetween and electrodes 113, 114 are fixedly attached to both ends of the actuator film 111. When a voltage is applied between the electrodes 113 and 114, current flows to the actuator film 111 to generate Joule heat and the film 111 expands or contracts. In this case, if the insulator film 112 uses a material having a thermal expansion coefficient smaller than that of the actuator film 111, the bonded film is warped due to the difference in the expansion coefficient between the surface and the rear face of the bonded films.

In Embodiment 4, a film of 30 μm thick comprising a mixed material of perfluorosulfonic acid-copolymer and fine carbon particles described in Embodiment 1 is used being formed into an U-shaped outer profile of 1 cm square as the actuator film 111. A polyimide film of 25 μm thick is used for the insulator film 112 and bonded with the actuator film 111 using an epoxy adhesive. When a voltage of 15 V is applied between the electrode 113 and electrode 114 of the actuator module 110, the top end of the film is warped downward by about 3 mm. The displacement at the top end of the film in this case is much greater than the displacement in the extending direction obtained by the actuator film explained for Embodiment 1. As described above, a larger displacement can be obtained in the bending actuator module.

Embodiment 5

Embodiment 5 proposes an example of applying the bending actuator module 110 explained for Embodiment 4 to a conveying device for conveying a light weight product such as paper, and an optical switching device for switching the optical channel of an optical fiber. This is to be explained with reference to FIG. 12 to FIG. 14. Further, an optical switching device using the actuator module of the V-structure explained for Embodiment 2 is also explained with reference to FIG. 15.

Figure 12A:
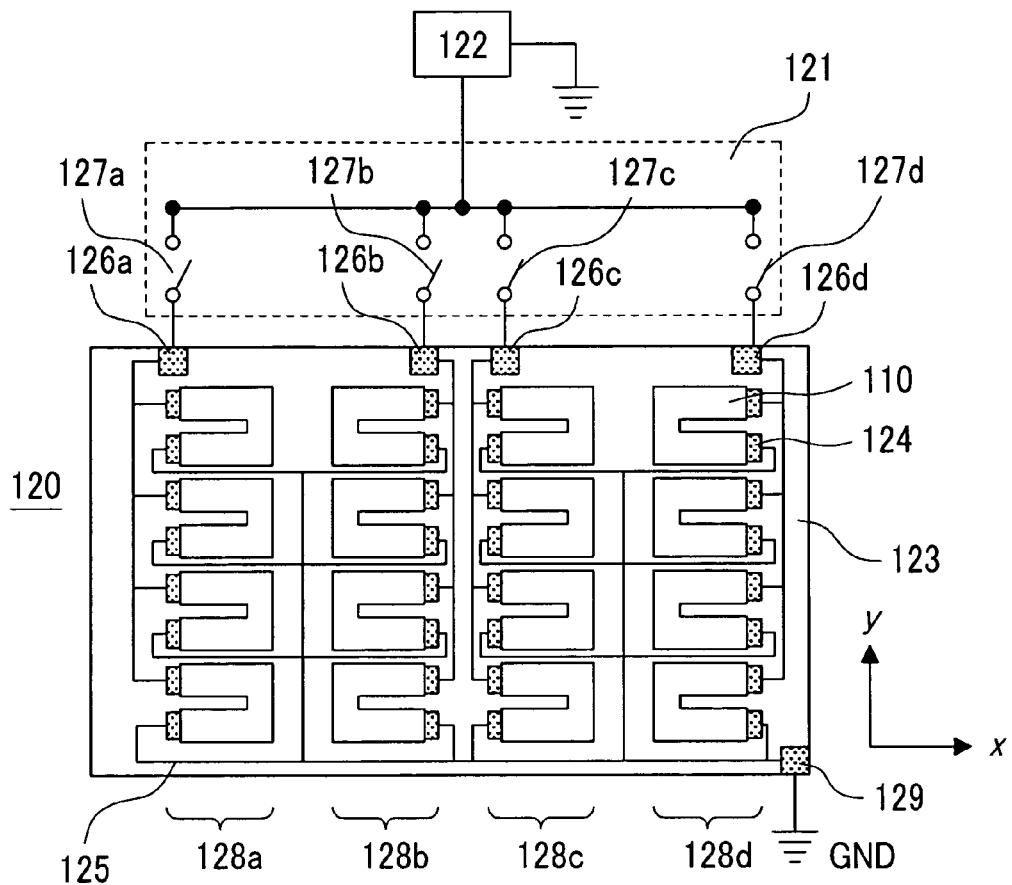
FIG. 12A is a schematic plan view illustrating the state of a conveying device 120 utilizing a plurality of bending actuator modules 110 described in Embodiment 4 and a convey system including a control circuit for operating the conveying device 120.
Figure 12B:
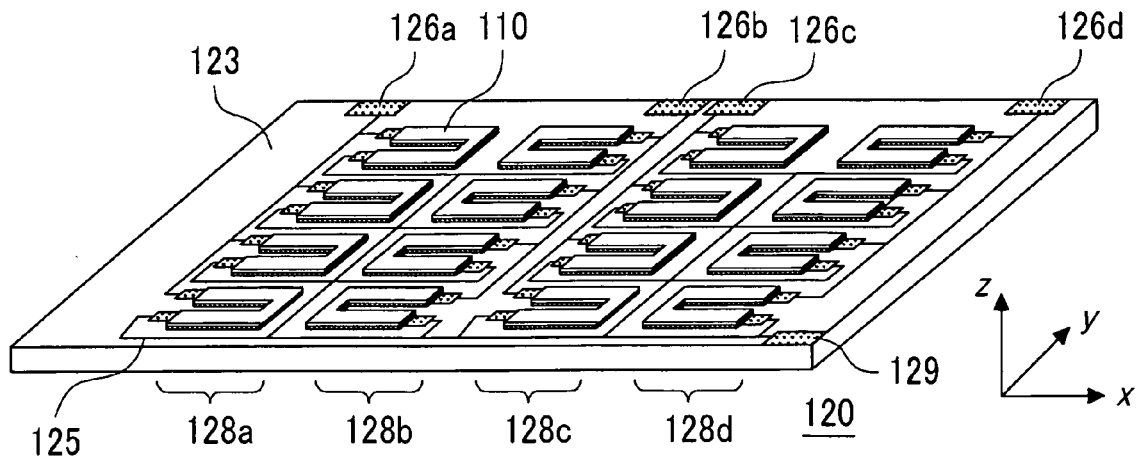
FIG. 12B is a perspective view of the conveying device 120 as viewed from obliquely above.

FIG. 12A is a schematic plan view, as shown from overhead, for the state of a conveying device 120 utilizing a plurality of the bending actuator modules 110 explained for Embodiment 4 and a conveying system also including a control circuit for operating the conveying device 120. FIG. 12B is a perspective view of the conveying device 120. The conveying system comprises the conveying device 120, a signal switching device 121, and a power control device 122. The conveying device 120 includes a substrate 123, bending actuator modules 110, metal electrodes 124, a wiring pattern 125, and voltage input terminals 126a, 126b, 126c, and 126d. The bending actuator modules 110 explained for Embodiment 4 each formed to an identical size are arranged in a 4×4 matrix on the substrate 123. The bending actuator modules 110 are arranged such that the direction of the U-shape is identical on every columns and the direction of the U-shape is inverted between adjacent rows to each other. Both ends of the actuator film surface of the bending actuator module 110 are electrically connected with metal electrodes 124 drawn on the substrate 123. Further, they are secured at the ends connected with the metal electrode 124 of the bending actuator module 110 to the upper surface of the substrate 123, and the surface of the insulator film 112 is on the upper surface of the substrate 123. The bending actuator modules 110 are eclectically connected in parallel on every columns by the metal electrode 124 and the wiring pattern 125. The bending actuator modules 110 are connected at terminals on one side with the voltage input terminals 126a, 126b, 126c, and 126d on every columns and at the terminals on the other side with the common ground terminals 129. The voltage input terminals 126a, 126b, 126c, and 126d are connected, respectively, by way of a signal switching device 121 comprising switches 127a, 127b, 127c, and 127d to the power control device 122.

In the arrangement shown in FIG. 12, when the actuator module 110 is bent, the top end displaces upward (in the direction apart from the upper surface of the substrate 123) opposite to that in FIG. 11B. That is, since it displaces in the direction z and in the direction x in the drawing, it conveys a material in the direction x. The conveying method of the material is to be described with reference to FIGS. 13A to 13E. A doted chain drawn through FIGS. 13A to 13E indicates the end face in the conveying direction where the conveyed product 130 situates initially.

Figure 13A:
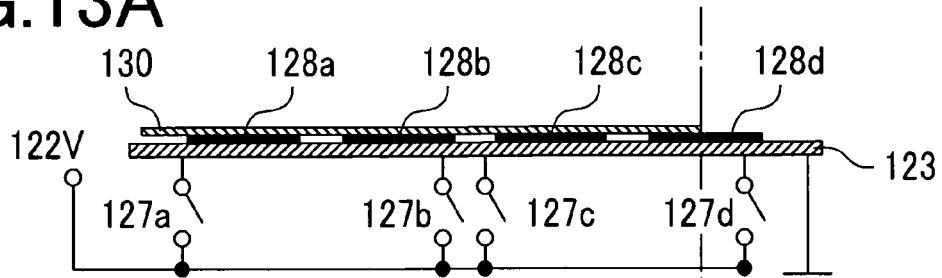
FIG. 13A illustrates a state where an electric current is not supplied to any of actuator columns of the conveying devices.
Figure 13B:
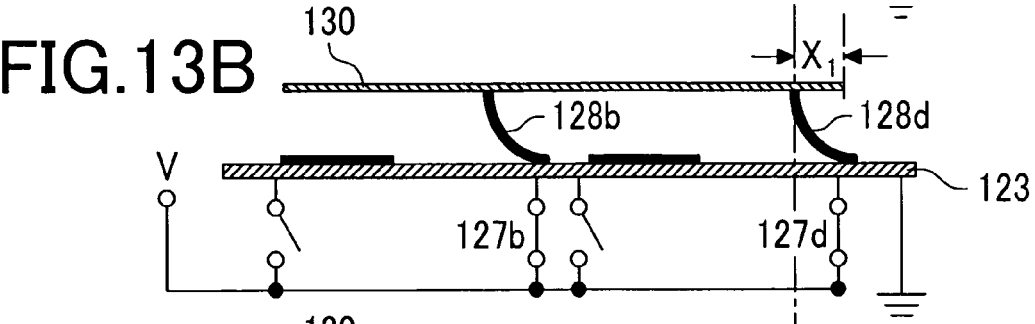
FIG. 13B illustrates the state where an electric current is supplied to an actuator column 128b and an actuator column 128d.
Figure 13C:
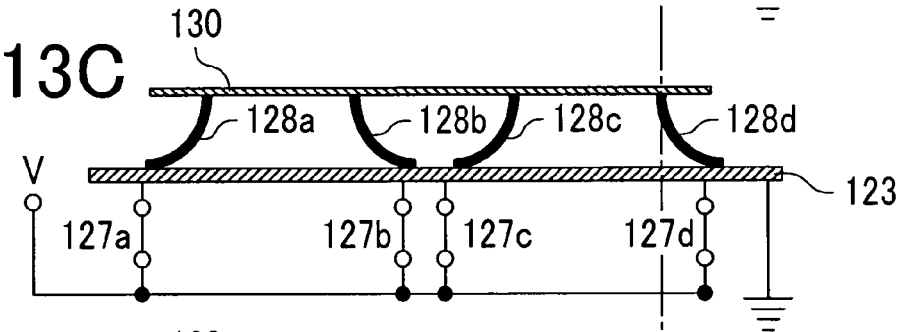
FIG. 13C illustrates the state where an electric current is supplied also to an actuator column 128a and an actuator column 128c from the state in FIG. 13B.
Figure 13D:
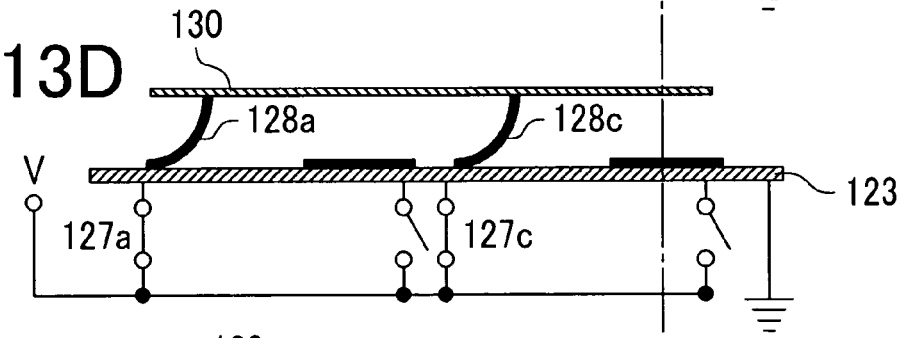
FIG. 13D illustrates the state where the electric supply is interrupted to the actuator column 128b and the actuator column 128d.
Figure 13E:
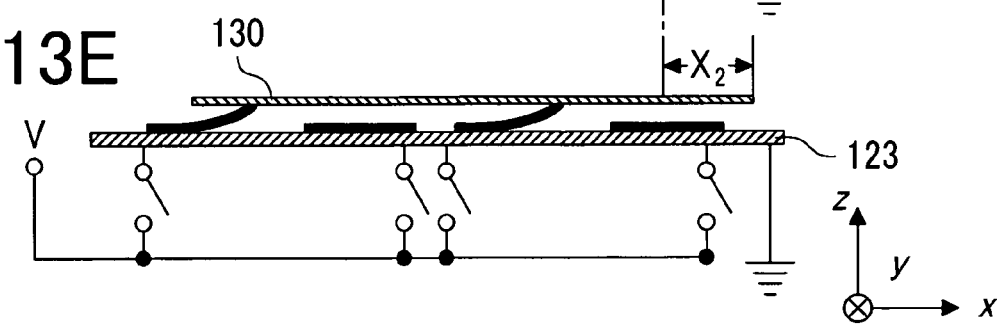
FIG. 13E illustrates the state just after electric supply is interrupted to all the actuator columns.

FIG. 13A shows a state in which none of the actuator columns 128a, 128b, 128c, and 128d arranged on the substrate 123 has any electric supply. A product to be conveyed 130 is placed over the plurality of actuator columns. FIG. 13B shows a state in which the switches 127b and 127d are turned on for electric supply to the actuator column 128b and the actuator column 128d. The actuator columns 128b and 128d under electric supply are bent upward and the product 130 is raised by the actuator column 128b and the actuator column 128d. In this case, since the direction of the displacement at the top end of the actuator is in the direction z and the direction x, the product to be conveyed 130 is raised (displacement in the direction z) and moved by $X_1$ in the direction x. FIG. 13C shows a state in which the switch 127a and 127c are turned on from the state in FIG. 13B, to conduct electric supply also to the actuator column 128a and the actuator column 128c to bend them upward like the actuator column 128b and the actuator column 128d. In this case, the product 130 is raised by all the actuator columns 128a, 128b, 128c, and 128d. Subsequently, as shown in FIG. 13D, electric supply to the actuator column 128b and the actuator column 128d are interrupted and the product 130 is supported by the actuator column 128a and the actuator column 128c. That is, the product 130 initially raised by the actuator column 128b and the actuator column 128d is supported by the actuator column 128a and the actuator column 128c. As shown in FIG. 12E, electric supply to the actuator column 128a and the actuator column 128c is interrupted subsequently. FIG. 12E shows a state just after interruption of electric supply. Bending of the actuator column 128a and the actuator column 128c is decreased in this state, and the top end of the actuator displaces in the direction −z and in the direction x. In accordance with the displacement at the top end, the conveyed product 130 lowers to the upper surface of the substrate 123 and also moves in the direction x. As a result, the end face of the product 130 moves from the initial position shown in FIG. 13A in the direction x by $X_2$. When the conveying system of Embodiment 5 is used, the product 130 can be conveyed in the direction x in the course shown in FIGS. 13A to 13E and repetition of the process will provide a large conveying distance. Since the bending actuator module according to the invention can be reduced in weight and reduced in size, a conveying device with a small occupying area and reduced in weight can be manufactured easily.

The conveying device described in FIG. 13 is useful for the conveyance of light weight products such as paper and, accordingly, applicable also to the conveyance of banknotes in ATM, conveyance of paper in printers, etc. In this case, since conveyance is not restricted only to the horizontal conveyance, in a case where two conveying devices shown in FIG. 13 are arranged so as to oppose on both sides of the conveying route to convey paper under pressing, vertical conveyance is also possible. In this case, it is necessary to displace the timing of voltage application such that when one of them changes from FIG. 13A to FIG. 13B, the other of them is in the state from FIG. 13D to FIG. 13E. This means that it can also cope with the conveyance along a curved surface so long as its radius of curvature can be sufficiently large.

Figure 14A:
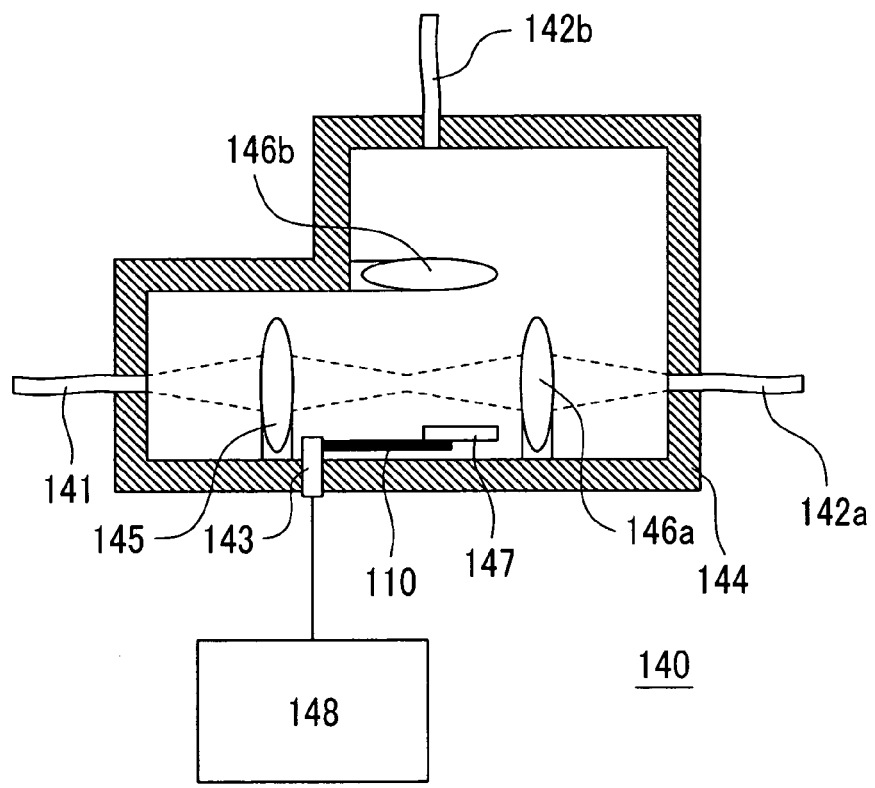
FIGS. 14A and 14B are diagrams showing other application mode of the bending actuator module shown in Embodiment 4.
Figure 14B:
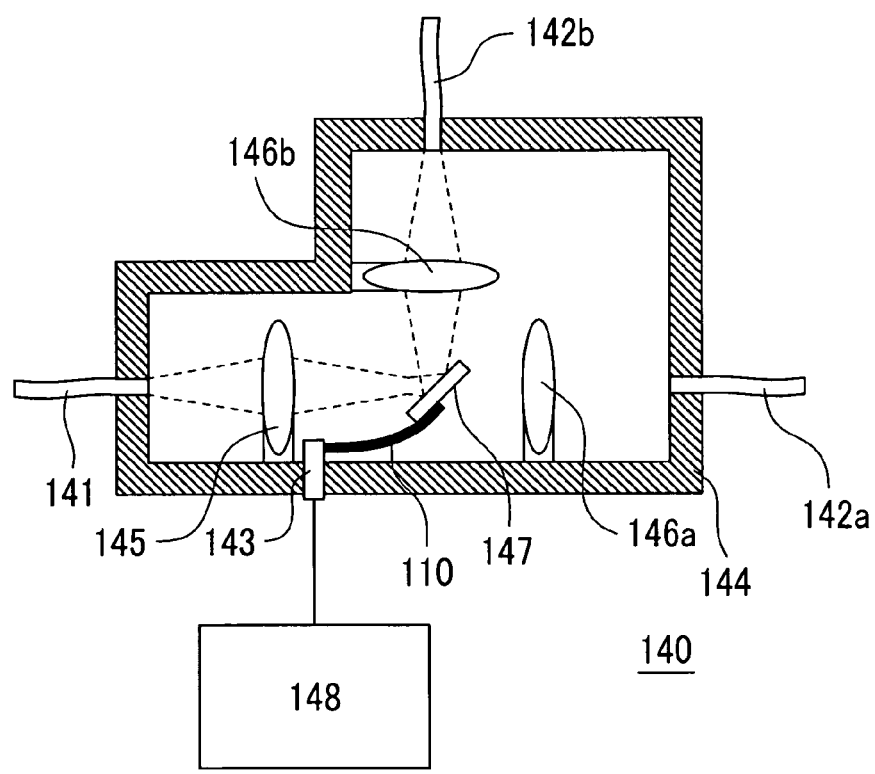

FIG. 14A and FIG. 14B are conceptional views showing an optical switching device for switching the optical channel of the optical fiber as another application embodiment of the bending actuator module shown in Embodiment 4. FIG. 14A shows, in cross section, a state of the optical switching device in which a voltage is not applied to the bending actuator module 110. FIG. 14B is a view showing in a cross section, a state of the optical switching device in a case where the voltage is applied to the bending actuator module 110, to bend the actuator thereby switching the optical channel.

An optical switching device 140 shown in Embodiment 5 includes a container 144 in which a system of light input optical fiber 141, two systems of output optical fibers 142a and 142b, and paired electrodes 143 for supplying a voltage to the actuator module are buried. The optical switching device 140 further includes an input light condensing lens 145, collimate lenses 146a, 146b, and a bending actuator module 110 described for Embodiment 4 joined with a minute mirror 147 contained in the container 144. A power control device 148 for supplying a voltage to the actuator module is connected with the paired electrodes 143 of the optical switching device 140. The bending actuator module 110 is fixed at the electrode portions on both ends to the container 144 and electrically connected with the electrodes 143. The minute mirror 147 is fixed to the end of the bending actuator module 110 on the side opposite to the electrode and changes the position and the angle in accordance with the bending of the actuator. Inside the container 144, the optical fiber 141 for light input, the lens 145 for condensing the incident light, the lens 146a for introducing the incident light by collimation to the light output optical fiber 142a, and the light output optical fiber 142a are arranged on a straight line. Further, the lens 146b and the light output optical fiber 142b for introducing the light reflected on the mirror 147 fixed at the top end of the bending actuator module 110 into the optical fiber 142b are arranged on a straight line.

As shown in FIG. 14A, the actuator is in a linear state before application of a voltage to the bending actuator module 110 and a light signal incident from the optical fiber 141 is introduced by way of lenses 145, 146a to an optical fiber 142a. That is, the optical signal is outputted from the optical fiber 142a. As shown in FIG. 14B, when a voltage is applied from the power control device 148 to the bending actuator module 110, the bending actuator module 110 is bent and the mirror 147 is inserted to the optical channel between the lenses 145 and 146a, and the light incident from the optical fiber 141 is reflected on the mirror 147 and introduced by way of the lens 146b to the optical fiber 142b. That is, the light signal is outputted from the optical fiber 142b. Since it is necessary that the angle of the mirror 147 is precise for introducing the light efficiently to the optical fiber 142b, a mechanism may be provided for fixing a small electromagnet to an appropriate portion of a support fixed to a wall surface inside the container 144, and fixing a minute soft magnetics (iron, silicon steal, etc.) to the mirror. Thus, the small soft magnetics fixed to the mirror are attracted to the electromagnet after movement thereof to the vicinity of a desired position, thereby enabling precise positioning. In a case of returning the position of the mirror, the voltage applied so far to the bending actuator module 110 is interrupted and the switch for the electromagnet is also turned off to release the same from the attraction state. Further, a member such as a stopper may be provided such that the bending actuator module 110 does not bend over a predetermined angle.

As described above, by the use of the optical switching device 140 of Embodiment 5, the light incident from the optical fiber 141 can be switched from the optical 142a to the optical fiber 142b. Since the bending actuator module of the invention can be miniaturized, an optical switch reduced in size, capable of being integrated and driven at a low voltage can be manufactured easily.

Figure 15A:
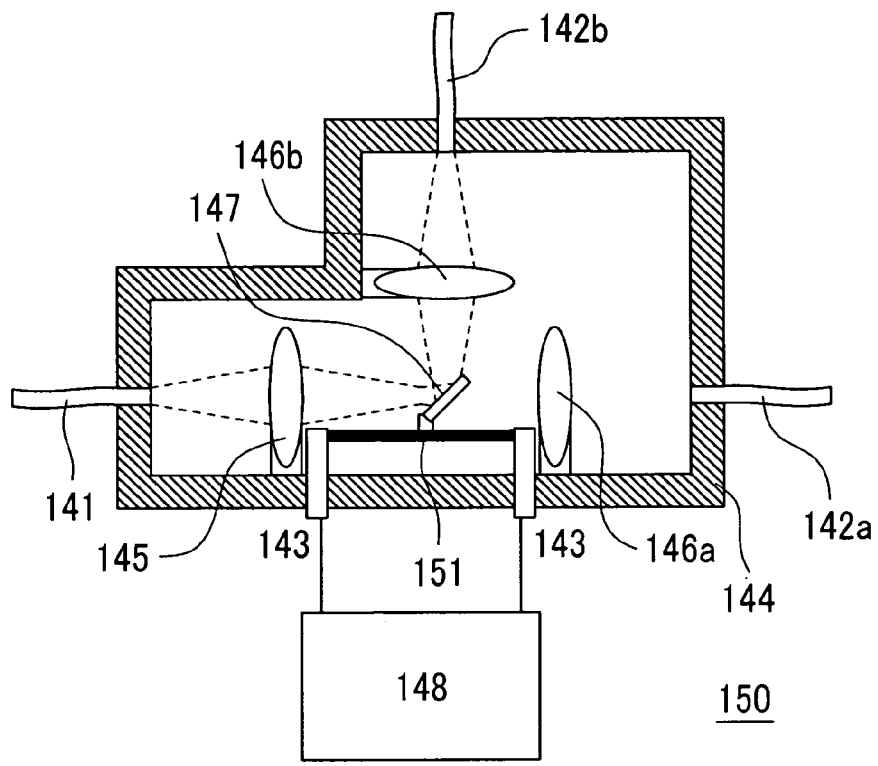
FIGS. 15A and 15B are conceptional diagrams showing an optical switching device 150 for switching the optical channel of an optical fiber as other application embodiment of the actuator module of the V-shape structure shown in Embodiment 2.
Figure 15B:
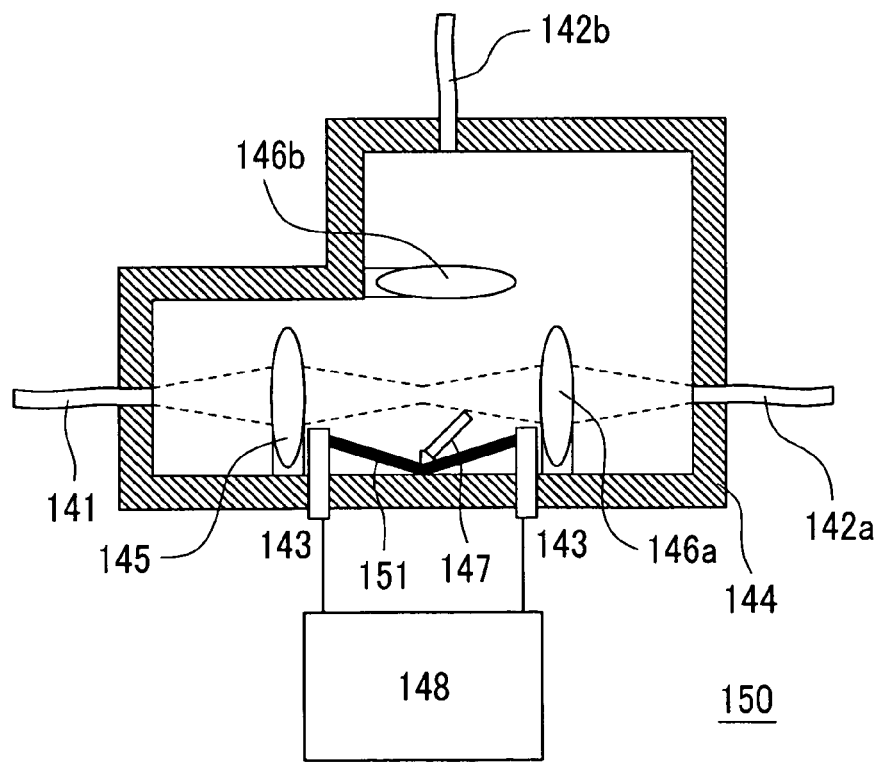

FIG. 15 is a conceptional view showing an optical switching device 150 for switching the optical channel of an optical fiber as other embodiment of applying the actuator module of the V-structure shown in Embodiment 2. FIG. 15A is a cross sectional view showing an optical switching device in a state where a voltage is not applied to the V-shaped actuator module 151. FIG. 15B is a cross sectional view showing the optical switching device in a state of applying the voltage on the V-shaped actuator module to distort the actuator and switch the optical channel. The optical switching device 150 is identical with the optical switching device 140 described in FIGS. 14A and 14B except for the portion of the actuator module provided with a mirror 147. The actuator module 151 included in the optical switching device 150 is fixed at both ends to paired electrodes 143 and the mirror tilted at an angle of 45° is attached to the central portion. In a state where a voltage is not applied to the actuator module 151, an optical signal input from the optical fiber 141 is reflected on the mirror 147 and output to an optical fiber 142b (FIG. 15A). When the voltage is applied to the actuator module 151, the actuator module 151 is extended. However, since the both ends of the actuator module 151 are fixed, the elongation for the change of the entire length thereof appears as a distortion in the vertical distortion. That is, the actuator module 151 is distorted and the mirror 147 attached to the central portion thereof moves downward by gravitational force. When the mirror 147 moves downward, the optical signal input from the optical fiber 141 is output straight to the optical fiber 142a. Thus, when the optical switching device 150 of Embodiment 5 is used, the light incident from the optical fiber 141 can be switched from the optical fiber 142b to the optical fiber 142a.

Embodiment 6

In Embodiment 6, a medical tube utilizing the bending actuator module described for Embodiment 4 and the actuator film described for Embodiment 1 is to be described with reference to FIG. 16 and FIG. 17.

Figure 16A:
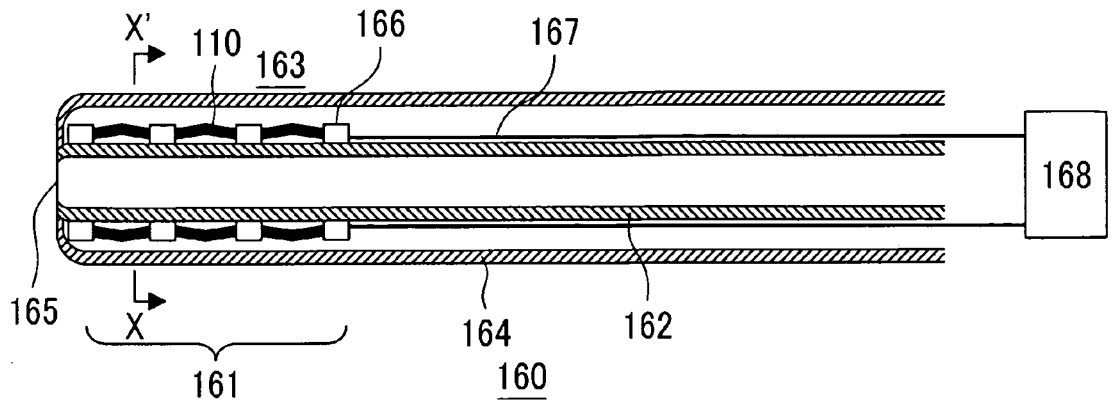
FIG. 16A is a schematic view illustrating a longitudinal cross sectional structure of a flexible tube 160 such as a catheter, as a medical tube.
Figure 16B:
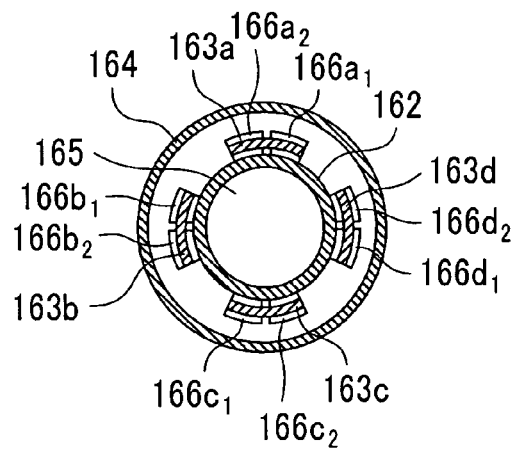
FIG. 16B is a schematic view for a cross sectional structure as viewed in the direction of arrows along X-X' in FIG. 16A.
Figure 16C:
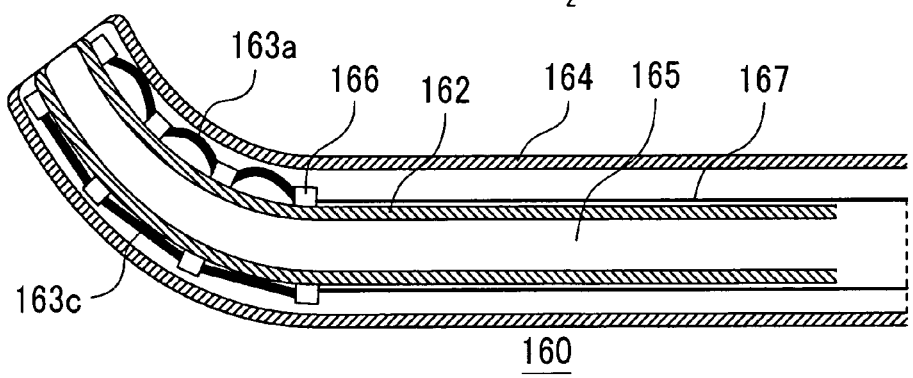
FIG. 16C is a schematic view of a cross sectional structure showing the state of bending a bend portion 161 in the flexible tube 160.
Figure 16D:
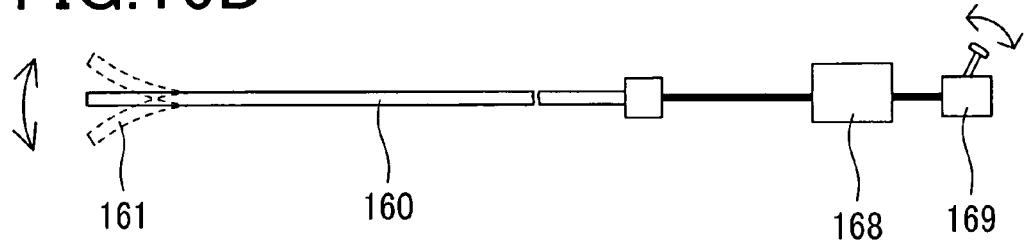
FIG. 16D is a conceptional view of a medical catheter system using the flexible tube 160.

FIG. 16A is a schematic view for a longitudinal cross sectional structure of a flexible tube 160 such as a catheter, etc. as a medical tube. FIG. 16B is a schematic view for a cross sectional structure along the direction of an arrow at X-X' in FIG. 16A. FIG. 16C is a schematic view for a cross sectional structure showing a state of bending a bent portion 161 in the flexible tube 160. FIG. 16D is a schematic view for a medical catheter system using the flexible tube 160.

As shown in FIG. 16A, the flexible tube 160 comprises a hollow tube 162 disposed axially centrally, four actuator units 163 disposed to the peripheral surface of the tube 162, and a cover 164 covering them. The top end of the flexible tube 160 is formed as a bent portion 161 bendable in an optional direction by external operation.

A hollow portion of the tube 162 is used for observation or treatment. Further, the tube is made of a soft and flexible and elastic material such as silicon rubber or polyurethane and can be bent freely by an external force. The cover 164 covers the tube 162 and the four actuator units 163 and is provided with an opening 165 at the top end.

Each of the actuator units 163 comprises a plurality of bending actuator modules 110 as described in Embodiment 4 which are connected linearly in the axial direction of the tube 162. The bending actuator modules 110 are fixed on both ends thereof, that is, at the end having the electrode 166 and at the end on the side opposite to the electrode 166 to the outer peripheral surface of the tube 162. In this case, the actuator film 111 formed into a U-shape and bonded with the insulator film 112 is fixed, in a slightly distorted state as shown in FIG. 16A when a voltage is not applied. Further, the bending actuator module 110 is fixed while selecting the surface thereof such that the distortion is increased upon application of the voltage. The bending actuator module 110 is joined with the electrode 166 disposed to the outer surface of the tube 162 and connected by way of a soft and flexible lead wire 167 joined therewith to a power control device 168 for applying a voltage to the bending actuator module.

As shown in FIG. 16B, the actuator units 163, i.e., four actuators units 163a to 163d are disposed along the outer periphery of the tube 162 at the bend portion 161. As shown in FIG. 11, since the electrodes 166 are disposed on both ends of the U-shaped actuator film, they are indicated here as $163a_1$, $163a_2$, $163b_1$, . . . . The lead wire 167 is not illustrated in FIG. 16B since this complicates the drawing.

For bending of the bend portion 161 of the flexible tube 160 in Embodiment 6, the actuator units 163 attached to the bend portion 161 are expanded or contracted. That is, when the actuator unit 163a is contracted and the actuator unit 163c disposed to the surface opposite to the actuator unit 163a is expanded, the bend portion 161 is bent such that the actuator unit 163a is in the inner side. The bend portion 161 can be bent freely in all directions if the actuator units 163 are attached at three or more positions along the outer periphery of the tube 162. FIGS. 16A and 16B show a case of providing the actuator units at 4 positions and, in this example, when an identical voltage is applied simultaneously to the actuator units 163a and 163b, the bend portion 161 can be distorted at an angle of 45° rightward in FIG. 16B.

To provide such bending, it is necessary that the displacement of the actuator unit be large. For this purpose, in the flexible tube 160 of Embodiment 6, a plurality of bending actuator modules 110 having large displacement and arranged linearly are used for the actuator unit 163. The bending actuator module 110 is bent upon application of a voltage and is in a linear form when the voltage is not applied. The change of the distance between both ends of the bending actuator modules along with the bending is much larger compared with the change of the distance between both ends of the actuator film when the actuator film described in Embodiment 1 is expanded and contracted by the application of an identical voltage. When the actuator unit 163 is constituted utilizing them, the displacement of the actuator unit 163 is increased.

In a case of forming the flexible tube 160 in a straight form as in FIG. 16A, the position of securing the bending actuator module 110 is controlled such that the bending actuator module 110 is in a slightly bent state. Alternatively, four actuator units may be fixed such that they are in a planer state and an identical voltage may be applied to each of them to attain a state where the bending actuator module 110 is slightly bent. This makes the length for each of the actuator units 163 identical and each of the bending actuator modules 110 does not undergo the tension from the tube 162 and the flexible tube 160 can be kept in a linear state.

As shown in FIG. 16C, when a high voltage is applied from the power control device 168 to the actuator unit 163a in the flexible tube 160 to greatly contract the actuator unit 163a and the bend portion 161 is bent without applying the voltage to the actuator unit 163c, the bend portion 161 is bent upward. The bending direction and the angle of bending of the flexible tube 160 can be controlled by applying a signal for designating the actuator unit to which the voltage is applied and the magnitude of the voltage to the power control device 168.

FIG. 16D is a schematic view for a medical catheter system using the flexible tube 160. The system includes a flexible tube 160, a power control device 168, and a bending operation device 169. The flexible tube 160 is connected electrically with the power control device 168. The power control device 168 is connected with the bending operation device 169 and applies a voltage to the actuator unit in the flexible tube 160 in accordance with the operation of the bending operation device 169 for designating the bending direction and the bending angle of the flexible tube 160 to thereby bend the bend portion 161 at the top end of the flexible tube 160. In this way, the flexible tube can be used as an active catheter by operating the same close at hand and bending it freely.

Figure 17A:
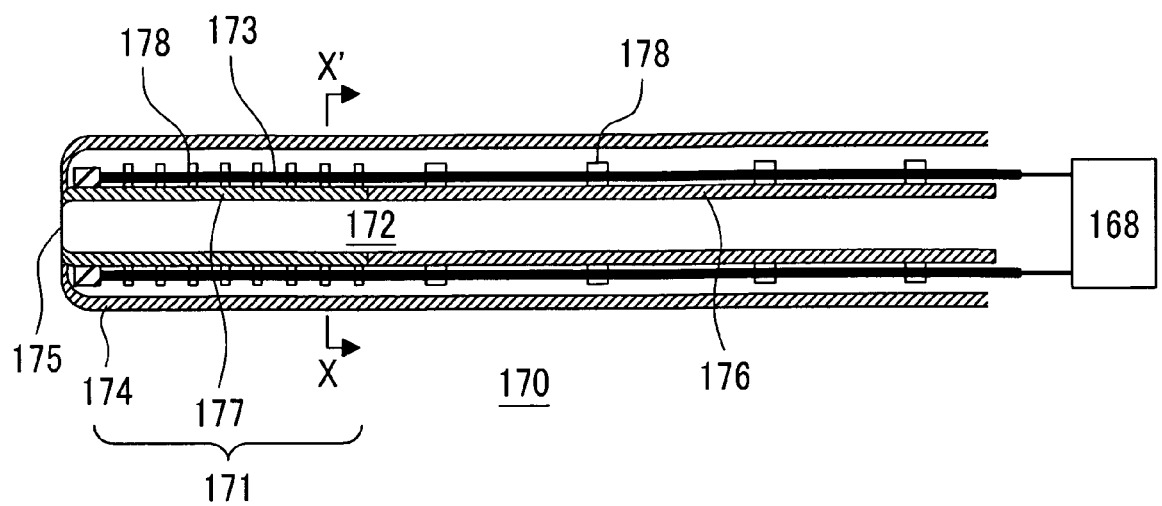
FIG. 17A is a schematic view of a longitudinal cross sectional structure of a flexible tube 170 such as a catheter, as a medical tube.
Figure 17B:
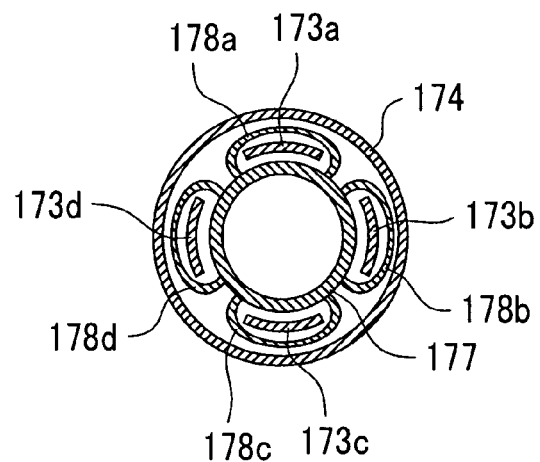
FIG. 17B is a schematic view of a cross sectional structure as viewed in the direction of arrows along X-X' in FIG. 17A.

Then, another embodiment of the medical tube utilizing the actuator of the invention is to be described with reference to FIGS. 17A and 17B. FIG. 17A is a schematic view for the longitudinal cross sectional structure of a flexible tube 170 for a catheter, etc. as a medical tube. FIG. 17B is a schematic view of a cross sectional structure along the direction of an arrow at position X-X' shown in FIG. 17A. The flexible tube 170, like the flexible tube 160 described for FIG. 16, includes a hollow tube 172 disposed in the central portion in the axial direction used for observation, treatment, etc., four actuator units 173a to 173d arranged along the peripheral surface of the tube 172, and a cover 174 covering them. An opening 175 is provided to the top end of the flexible tube 170, and the top end of the flexible tube 170 constitutes a bend portion 171 bendable in the optional direction by the external operation.

The tube 172 comprises a base tube 176 made of a soft and flexible material such as silicon rubber or polyurethane, and a bend tube 177 connected at the top end thereof. The bend tube 177 is made of a material more flexible than the base tube 176 and can be bent freely by an external force easily.

The flexible tube 170 and the flexible tube 160 are different each other mainly with respect to the actuator unit. In the flexible tube 160, the displacement of the actuator unit 163 is increased by utilizing the bending actuator module whereas in the flexible tube 170, an actuator unit 173 utilizing the actuator film described in Embodiment 1 is used instead of the bending actuator module. However, the actuator film described in Embodiment 1 has a smaller strain, i.e., a less ratio of the displacement of the film relative to the entire length of the film. Accordingly, the amount of displacement is increased by arranging the actuator units 173 along the axial direction of the flexible tube 170 thereby increasing the entire length.

The actuator units 173a to 173d are bounded by the guides 178a to 178d attached to the outside of the tube 172. Then, the actuator units 173 are movable in the axial direction of the tube 172 but are restricted from movement in the radial direction. The distance between each of the guides 178a to 178d is made shorter at the position for the bend tube 177 than that at the position for the base tube 176. Further, both ends of the actuator unit 173 are fixed to both ends of the tube 172. A voltage from the power control device 168 can be applied by way of a soft and flexible lead wire 167 to the both ends of each actuator unit 173. As described above for Embodiment 1, the actuator unit 173 applied with the voltage is contracted. Accordingly, the bend tube 177 is bent such that the contracted actuator unit 173 is on the inner side. Since the plurality of actuator units 173 are provided (by the number of four in FIGS. 17A and 17B) along the peripheral surface of the bend tube 177, when an actuator unit 173 to be applied with the voltage is determined in accordance with the direction desired to bend the flexible tube 170 and the voltage is applied thereto, the bend portion 171 of the flexible tube 170 can be bent in all directions freely as in the case of the flexible tube 160. Accordingly, as described for FIG. 16D, the bend portion 171 of the flexible tube 170 can be bent freely in response to the electric signals.

In FIG. 17, while the electrodes are attached to both ends of the actuator film 1, when the resistance of the actuator film is high, no sufficient operation can be expected unless the voltage of the power source is high. Accordingly, the power source voltage can be kept low by attaching a plurality of electrodes in the midway of the actuator film to operate the same in parallel.

Since the actuator module according to the invention is reduced in weight and miniaturized in size, a medical tube small in size and reduced in weight can be manufactured easily by utilizing the same.

Reference numerals used in the drawings of this specification are listed as follows:

1 . . . actuator film, 2 . . . polymer material, 3 . . . fine conductive particles, 4 . . . power source, 5 . . . switch, 6 . . . electrode, 7 . . . electrode, 8 . . . load, 10 . . . actuator material, 11 . . . polymer, 12 . . . solvent, 13 . . . fine conductive particles, 14 . . . mixed solution of polymer and fine conductive particles, 15 . . . substrate, 16 . . . film comprising a mixture of polymer and the conductive particles, 17 . . . purified water, 21 . . . substrate, 22 . . . mold, 60 . . . actuator module, 61 . . . actuator film, 62 . . . electrode, 63 . . . electrode, 64 . . . stretching member, 65 . . . container, 66 . . . pin, 70 . . . actuator module, 71 . . . actuator film, 72 . . . electrode, 73 . . . electrode, 74 . . . container, 75 . . . hole, 76 . . . lid, 77 . . . spring, 78 . . . pin, 90 . . . Braille display device, 91 . . . Braille display system, 92 . . . Braille display terminal, 93 . . . control and instruction device, 94 . . . driving signal generation device, 100 . . . Braille display device, 101 . . . Braille display system, 102 . . . Braille display terminal, 110 . . . bending actuator module, 111 . . . actuator film, 112 . . . insulator film, 113 . . . electrode, 114 . . . electrode, 120 . . . conveying device, 121 . . . signals switching device, 122 . . . power control device, 123 . . . substrate, 124 . . . metal electrode, 125 . . . wiring pattern, 126a-d . . . voltage input terminal, 127a-d . . . switch, 129 . . . ground terminal, 130 . . . product to be conveyed, 140 . . . optical switching device, 141 . . . light inputting optical fiber, 142a . . . light outputting optical fiber, 142b . . . light outputting optical fiber, 143 . . . paired electrode, 144 . . . container, 145 . . . input light condensing lens, 146a . . . collimate lens, 146b . . . collimate lens, 147 . . . mirror, 148 . . . power control device, 150 . . . optical switch, 151 . . . actuator module, 160 . . . flexible tube, 161 . . . bend portion, 162 . . . tube, 163 actuator unit, 164 . . . cover, 165 . . . hole, 166 . . . electrode, 167 . . . lead wire, 168 power control device, 169 . . . bend portion operating device, 170 . . . flexible tube, 171 . . . bend portion, 172 . . . tube, 173 actuator unit, 174 . . . cover, 175 . . . hole, 176 . . . base tube, 177 . . . bend tube, 178 . . . guide

What is claimed is:

1. An actuator comprising:
a molding product of a material comprising a mixture of fine conductive particles and a polymer material, the material expanding or contracting by electric supply; and
at least two electrodes for electric supply disposed on both side portions of the molding product which expands or contracts.

2. An actuator according to claim 1, wherein the molding product deforms by thermal expansion or thermal contraction accompanying heat generation by Joule heat caused by an electric current flowing between the electrodes formed at the molding product.

3. An actuator according to claim 1, wherein an amount of deformation of the actuator is controlled by adjusting a voltage applied between the electrodes.

4. An actuator according to claim 1, wherein the actuator performs a function of the actuator by use of a load that the actuator undergoes.

5. An actuator according to claim 1, wherein the material has a coefficient of a linear thermal expansion of 0.00001 to 0.001/K within a temperature range from 100° C. to 200° C., an electric conductivity of from 0.1 to 1000 S/cm within a temperature range from 100° C. to 200° C., and a specific gravity of from 0.5 to 5 within a temperature range from 100° C. to 200° C.

6. An actuator according to claim 1, wherein the material has a tensile strength of from 0.3 MPa to 200 MPa within a temperature range from 100° C. to 200° C.

7. An actuator according to claim 1, wherein the material has a coefficient of linear thermal expansion of from 0.00005 to 0.0002/K within a temperature range from 100° C. to 200° C.

8. An actuator according to claim 1, wherein the material has an electric conductivity of from 0.1 to 100 S/cm within a temperature range from 100° C. to 200° C.

9. An actuator according to claim 1, wherein the material has a specific gravity of from 0.5 to 5 within a temperature range from 100° C. to 200° C.

10. An actuator according to claim 1, wherein the material has a tensile strength of from 1 MPa to 100 MPa within a temperature range from 100° C. to 200° C.

11. An actuator according to claim 1, wherein the current upon electric supply to the molding product is restricted such that the temperature of the molding product can be kept to the glass transition temperature of the material or lower.

12. An actuator according to claim 1, wherein the fine conductive particles comprise a fine conductor of fine carbon particles, fine platinum particles, fine gold particles, fine silver particles, fine nickel particles, fine copper particles, carbon nanotubes or a mixture thereof.

13. An actuator according to claim 1, wherein the polymer is perfluorosulfonic acid-copolymer, acrylonitrile-butadiene-styrene resin, polymethyl methacrylate such as acrylic resin, polyethylene terephthalate, polyamide, polyoxymethylene, polytetrafluoroethylene, polystyrene, polycarbonate, polyalkenes such as polycyclohexylethylene, polyacrylic acid, or polymethacrylic acid.

14. An actuator module comprising:
   an actuator film of a material comprising a mixture of fine conductive particles and a polymer material, the material expanding or contracting by electric supply; and
   at least two electrodes for electric supply disposed on both side portions of the actuator film which expands or contracts;
   wherein the actuator film and the two electrodes are housed in a predetermined container.

15. An actuator module according to claim 14, wherein the two electrodes of the actuator film are respectively fixed to opposing inner surfaces of the container, and
   a load is coupled to a central portion of the actuator film to render the actuator film always put under tension.

* * * * *